US011726217B2

(12) United States Patent
De Jean et al.

(10) Patent No.: US 11,726,217 B2
(45) Date of Patent: Aug. 15, 2023

(54) SYSTEMS AND METHODS FOR MEASURING AND TRACKING ENERGY EMITTED BY A RADIATION SOURCE

(71) Applicant: Luca Medical Systems, Inc., Palo Alto, CA (US)

(72) Inventors: Paul De Jean, Palo Alto, CA (US); Elliot Grafil, Palo Alto, CA (US); Cesare Jenkins, Palo Alto, CA (US); Tae Jin Kim, Palo Alto, CA (US)

(73) Assignee: Luca Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 17/483,343

(22) Filed: Sep. 23, 2021

(65) Prior Publication Data

US 2022/0091283 A1    Mar. 24, 2022

Related U.S. Application Data

(60) Provisional application No. 63/082,213, filed on Sep. 23, 2020.

(51) Int. Cl.
*G01T 1/20*    (2006.01)
(52) U.S. Cl.
CPC .......... *G01T 1/2006* (2013.01); *G01T 1/2002* (2013.01)
(58) Field of Classification Search
CPC .................. G01T 1/2006; G01T 1/2002
See application file for complete search history.

(56) References Cited

U.S. PATENT DOCUMENTS

| 5,864,146 A * | 1/1999 | Karellas ............... A61B 6/4258 378/191 |
|---|---|---|
| 2004/0210132 A1 | 10/2004 | Manjeshwar |
| 2009/0116720 A1 | 5/2009 | Ritman |
| 2012/0029263 A1 | 2/2012 | Wardt et al. |
| 2014/0018675 A1 | 1/2014 | Keppel et al. |
| 2014/0306116 A1 | 10/2014 | Roessl et al. |
| 2015/0076357 A1 | 3/2015 | Frach |
| 2017/0276809 A1 | 9/2017 | Smith |

FOREIGN PATENT DOCUMENTS

DE    102018133601 A1    7/2020

OTHER PUBLICATIONS

"International Search Report and Written Opinion Received for PCT Application No. PCT/US21/51753," dated Jan. 27, 2022, 9 Pages.

* cited by examiner

*Primary Examiner* — Hugh Maupin
(74) *Attorney, Agent, or Firm* — Terrence J. Edwards; TechLaw Ventures, PLLC

(57) ABSTRACT

Measuring and tracking energy emitted by a radiation source. A system includes an image sensor for sensing electromagnetic radiation and a scintillator. The scintillator absorbs energy emitted by a radiation source and scintillates the absorbed energy. The system is such that the image sensor senses an image frame depicting at least a portion of the scintillator when the radiation source emits the energy. The image frame comprises an indication of where the energy is absorbed by the scintillator.

20 Claims, 13 Drawing Sheets

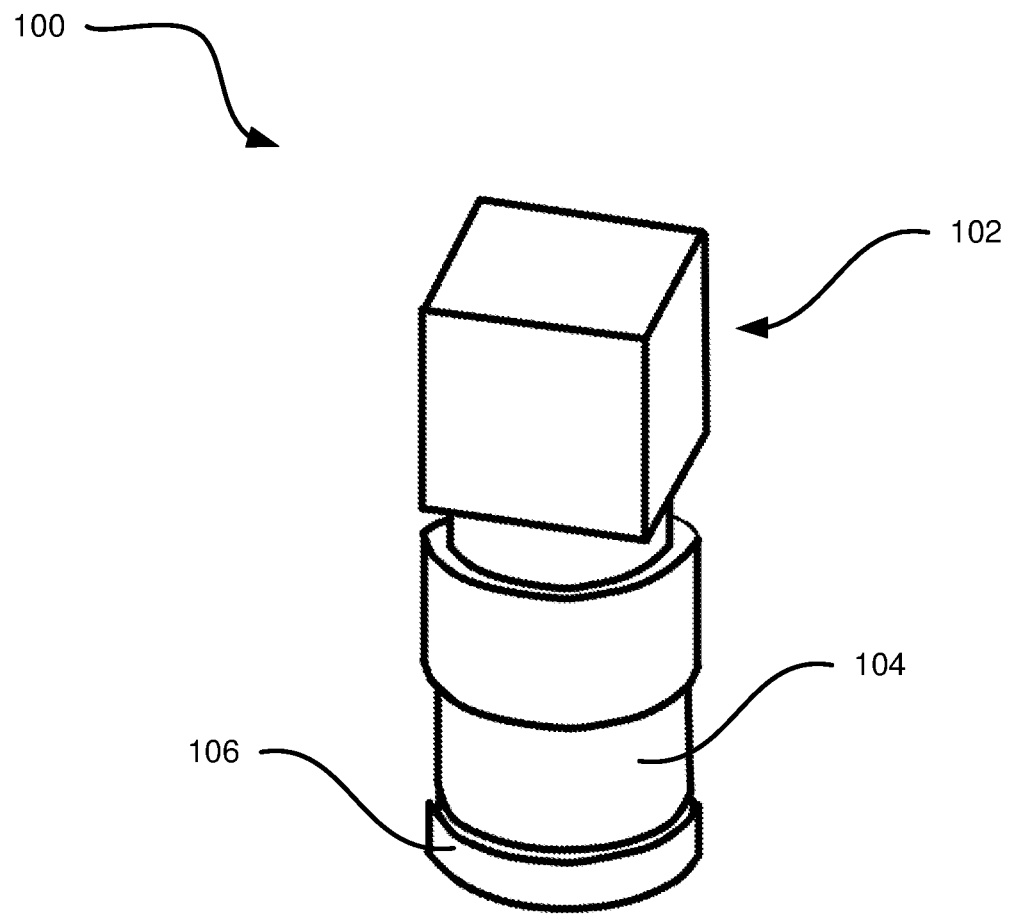
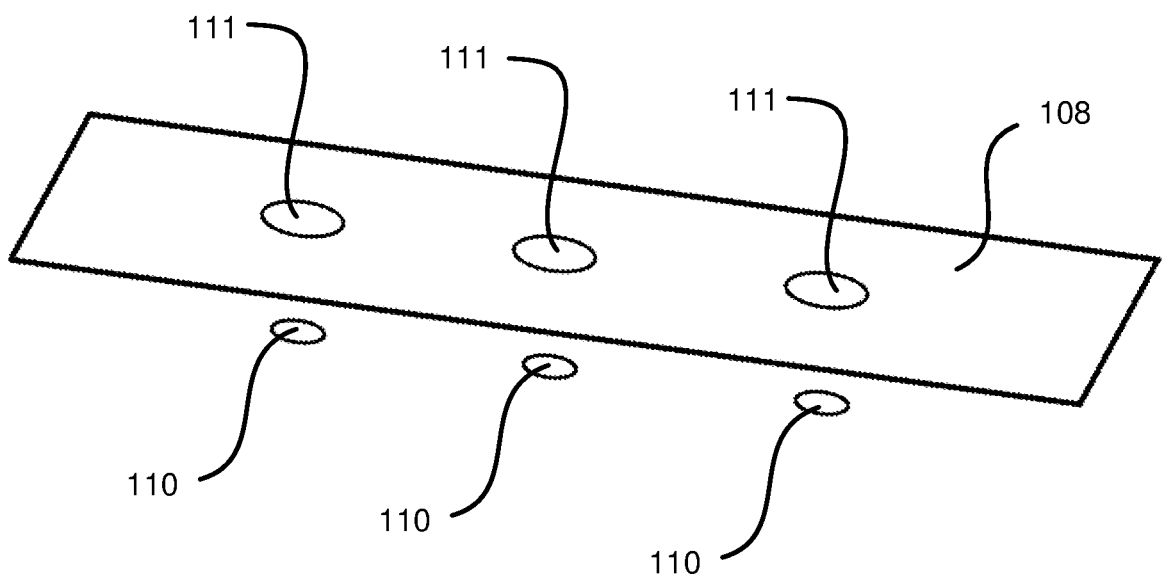
FIG. 1

```
┌─────────────────────────────────────────────────────────────────────────────┐
│ Calculating A Contrast-To-Noise Ratio Of An Image Frame. Calculating Pixel   │
│ Intensity Values For A Plurality Of Pixels In The Image Frame.               │
│                                   1002                                       │
└─────────────────────────────────────────────────────────────────────────────┘
                                      ↓
┌─────────────────────────────────────────────────────────────────────────────┐
│                  Applying An Adaptive Threshold To The Histogram.            │
│                                   1004                                       │
└─────────────────────────────────────────────────────────────────────────────┘
                                      ↓
┌─────────────────────────────────────────────────────────────────────────────┐
│ Extracting Contours Of A Region Of Interest In The Image Frame, Wherein The  │
│ Region Of Interest Comprises A Scintillating Region Wherein A Scintillator   │
│ Is Scintillating Energy Emitted By A Radiation Source.                       │
│                                   1006                                       │
└─────────────────────────────────────────────────────────────────────────────┘
                                      ↓
┌─────────────────────────────────────────────────────────────────────────────┐
│              Identifying A Geometric Center Of The Region Of Interest.       │
│                                   1008                                       │
└─────────────────────────────────────────────────────────────────────────────┘
```

FIG. 10

SYSTEMS AND METHODS FOR MEASURING AND TRACKING ENERGY EMITTED BY A RADIATION SOURCE

CROSS-REFERENCE TO RELATED APPLICATION

This application claims the benefit of U.S. Provisional Patent Application No. 63/082,213, filed Sep. 23, 2020, entitled SYSTEMS AND METHODS FOR MEASURING AND TRACKING RADIATION SOURCES. The aforementioned patent application is incorporated herein by reference in its entirety, including but not limited to those portions that specifically appear hereinafter, the incorporation by reference being made with the following exception: In the event that any portion of the above-referenced provisional patent application is inconsistent with this application, this application supersedes the above-referenced patent application.

TECHNICAL FIELD

The disclosure relates generally to radiation detection and specifically to extracting spatial, temporal, and intensity information from radiation sources.

BACKGROUND

Radiation includes energy that is released in the form of rays or high-speed particles. Atoms may decay and release energy in the form of radiation as the atoms strive to transition from an unstable state to a more stable state. There are different forms of radiation that exist in nature. Broadly speaking, radiation can be characterized as electromagnetic radiation and particle radiation. Particle radiation includes the emission of fast moving particles that have both energy and mass associated with their release. This form of radiation may include alpha particles, beta particles, and neutrons.

Radiation can further be characterized as ionizing radiation or non-ionizing radiation. The distinction between ionizing radiation and non-ionizing radiation relates to what the radiation has the capacity to do when the radiation passes through matter or is incident on a material. Non-ionizing radiation can transfer energy into a material through which it passes, but because it has relatively low energy, non-ionizing radiation cannot break molecular bonds that exist in the material or cause electrons to be removed from the atoms in the material. Ionizing radiation, however, can impart enough energy to the material to break molecular bonds and strip electrons from the atoms in the material. When electrons are removed from an atom, the result is the creation of ions. Ions can be hazardous to living cells in plants and animals. Common types of ionizing radiation include both particle radiation and electromagnetic radiation, wherein the specific emission types include alpha particles, beta particles, neutrons, X-Rays, and gamma rays.

In some cases, radiation is intentionally supplied to biological tissue or other substances. One example of such a procedure is brachytherapy, wherein radioactive material is placed within a body cavity or otherwise supplied to biological tissue. Brachytherapy may be implemented to treat cancer and may alternatively be referred to as "internal radiation." Brachytherapy enables practitioners to deliver higher doses of radiation to specific regions of the body, compared with the conventional form of radiation therapy (external beam radiation) that projects radiation from a machine external to the body. Brachytherapy is used to treat numerous types of cancer and may be used alone or in conjunction with additional cancer treatments. Radiation therapy is inherently high-risk, and in some cases, it is imperative that the correct amount of radiation is supplied to the biological tissue.

Brachytherapy and other forms of radiation therapy are used in connection with radiation detectors. Radiation detectors, which may also be referred to as radiation sensors, are instruments that sense and measure radiation emissions or levels of radiation produced by a source. Radiation detectors may measure, for example, the specific energy levels of the radiation (in kV or MV), the counter per unit time (in minutes or seconds), the number of Roentgens in the air per unit of time, the dose rate (in grays (joules/kg) or rads per unit time), the total accumulated dose (in grays or rads), and the biological risk of exposure to radiation (in rem or sievert).

Brachytherapy and other radiation procedures can be effective for delivering a precise amount of radiation to a precise region. However, it is challenging to be certain that the radiation procedure is being performed correctly and ensuring that the correct amount of radiation is delivered to the correct region. Therefore, what is needed are systems, methods, and devices for measuring and tracking the energy emitted by a radiation source.

In light of the foregoing, disclosed herein are systems, methods, and devices for measuring and tracking the energy emitted by a radiation source. The systems, methods, and devices described herein enable quality assurance for radiation procedures.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where:

FIG. 1 is a schematic diagram of a system for measuring and tracking energy emitted by a radiation source, wherein the system includes an imager assembly for acquiring the coordinates and time stamps of one or more radiation emissions;

FIG. 6 is a schematic diagram of a placement assembly for calibrating a coordinate grid on an image sensor to the coordinate space of the channel the radiation source passes through;

FIG. 10 is a schematic flow chart diagram of a method for identifying a geometric center of a region of interest in an image frame;

DETAILED DESCRIPTION

Figure 2:
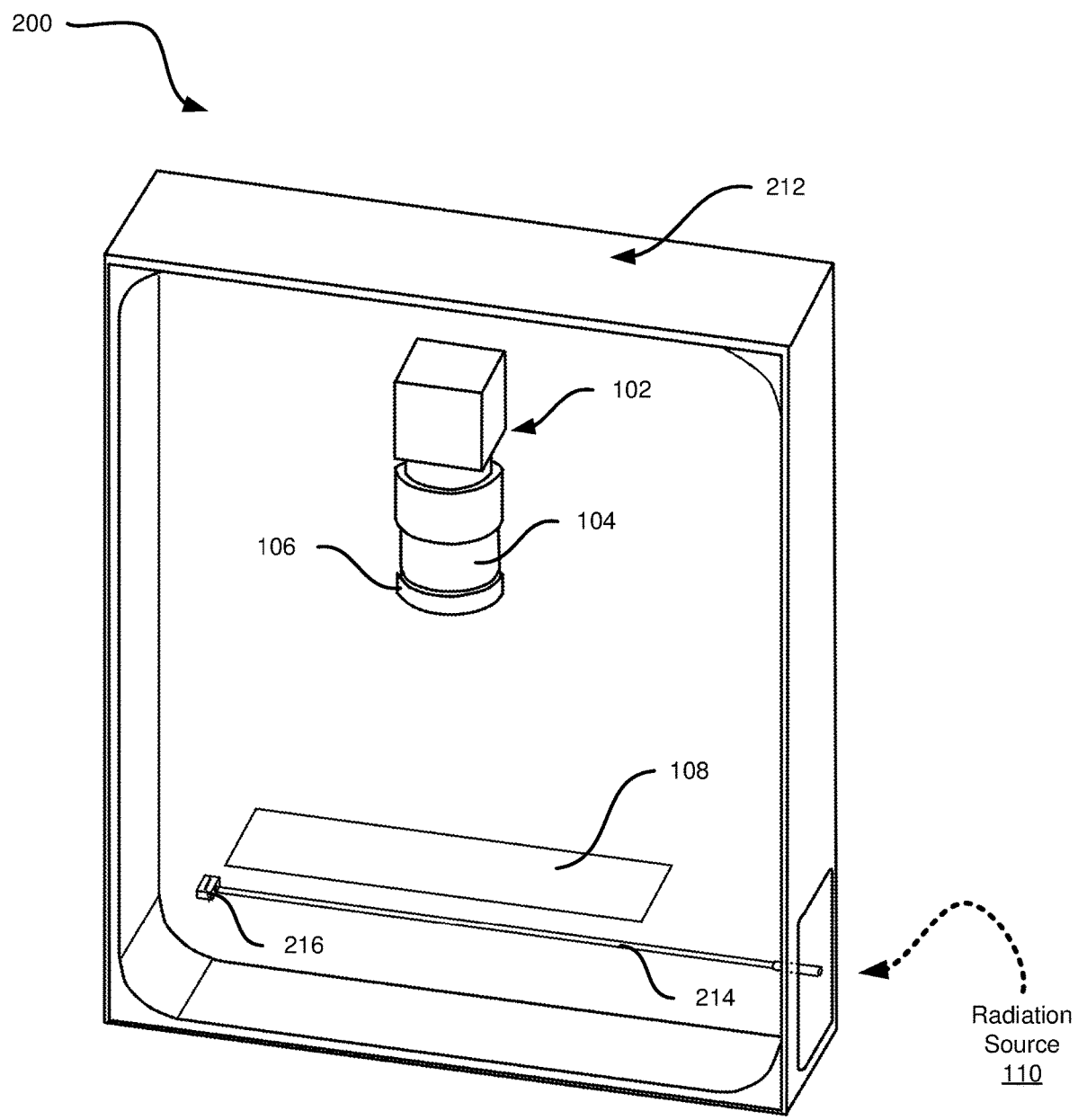
FIG. 2 is a schematic diagram of a system for measuring and tracking energy emitted by a radiation source, wherein the system includes a single-channel placement system.

Disclosed herein are systems, methods, and devices for measuring and tracking energy emitted by one or more radiation sources for use in medical and non-medical applications. Specifically disclosed herein are means for directly extracting spatial, temporal, and intensity information for emissions of radiation energy based on image frame data.

The systems, methods, and devices described herein are configured for tracking a stationary or moving radiation source and mapping the results into a Cartesian or Polar coordinate system as a function of time. This is performed while simultaneously providing relative radioactivity information.

One application of the disclosure is for quality assurance (QA) in brachytherapy. Brachytherapy is an internal radiation therapy technique that treats malignant tumor sites by directly positioning radioactive seeds within the patient's body. Over the years, technologies such as remote afterloaders and electronic mini X-Ray sources have been developed to enhance treatment accuracy while minimizing exposure to unwanted radiation. Quality assurance is an important procedure in radiation therapy to ensure the consistency of prescribed radiation doses from such systems.

Traditional quality assurance technologies for radiation therapies have remained essentially the same over time. Most quality assurance systems employ radiochromic film for positional accuracy, stopwatch timing for temporal accuracy, and well chambers for measuring the radioactivity of the source of radiation in the brachytherapy system. Some existing commercial systems track marker wire or simulator wire and radioactive seed position using digital photography. However, the typical quality assurance processes known in the art still require employing manual tools such as stopwatches for time measurement and rulers for position measurement. In addition, the current methods fail to provide automated data acquisition, digitization of data, robust data management, and automatic report generation of the quality assurance results. The current workflow is laborious and current methods limit the overall accuracy of the quality assurance process. This causes difficulty in accessing the complete quality assurance history. Therefore, there is a need for an autonomous solution that can robustly and accurately complete multiple quality assurance procedures while historically tracking data.

Before the structures, systems, and methods for measuring and tracking radiation sources for use in medical and non-medical applications are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Disclosed herein are automated systems for acquiring spatial, temporal, and intensity measurements of radiation sources. Spatial measurements include accurately measuring the position of a radiation source. Temporal measurements include accurately measuring the time the radiation source stays at a specific position. Intensity measurements include the accurate measurement of the radioactive signal emitted by the radiation source. Thus, the systems, methods, and devices described herein can identify radiation, measure where the radiation is located, identify how long the radiation is detected, and calculate how much radiation is required to make the scintillator emit light.

Broad applications of the disclosure include, but are not limited to, radiation safety and quality assurance in medical systems where radiation sources are employed. Applications in radiation safety include but are not limited to analysis of contaminated materials. Applications in medical systems include, but are not limited to, radiation therapy machine quality assurance, radiation therapy patient quality assurance, tracking radiation source location inside of patients, and nuclear medicine radioactive materials analysis.

The embodiments of the disclosure include an acquisition unit, a computer, and software. In some embodiments, a computer is integrated inside the acquisition unit for a single-body system, but in others, it is connected externally via a data transfer cable or using wireless communications. The acquisition unit is comprised of an imager assembly, mounting components, and an optional source placement system. The source placement is a passageway of any form that allows entry of radiation sources into the acquisition unit. In some embodiments, the imager assembly is comprised of any number of optical cameras, lenses, and scintillators. In some embodiments, the acquisition unit is designed to be compact, wherein a single person can transport the system within the nuclear facility or clinic.

Some embodiments of the disclosure include automated systems for brachytherapy or internal radiation therapy machine and patient quality assurance. The present disclosure applies to all available radiation sources used in low, medium, and high-dose brachytherapy, which include, but not limited to, Cs-131, Pd-103, I-125, Co-60, Ir-192, etc.

An implementation of the disclosure is used as a brachytherapy machine quality assurance system. The acquired data consists of the source dwell position, source dwell time, and source radioactivity by measuring the radiation source delivered by the brachytherapy system. In some aspects of the disclosure, the source placement system connects to a clinical remote high dose-rate afterloader via a clinical transfer guide tube. An afterloader is a motorized system that remotely drives the radiation source into the patient with precise positioning and timing. In some embodiments, the source placement system includes fiducial markers and/or internal lighting to register the absolute position of the source with the coordinate system of the imager assembly. The source placement system has a flexible design to allow fluid insertion of radiation sources. In one aspect, the disclosure provides information on the wire or source velocity to report the state and/or condition of the internal motor within the afterloader system. In another aspect, the disclosure provides information on the position of the source to determine the state and/or condition of the internal motor and its associated encoder within the afterloader system. In another aspect, the disclosure provides information on the time the source spends at a particular, fixed location to determine the state/condition of the timing hardware. In another aspect, the disclosure provides position and time information of the source during a procedure that is interrupted by an emergency stop or other event to measure if the correct position is prescribed before and after the event, and if the total dwell time is accurate across the interruption. In another aspect, the acquisition unit has multiple source placement systems incorporated to allow individual connection with multiple transfer guide tubes from the remote afterloader. In some embodiments, a transparent source placement system sits adjacent to the scintillator, and it is possible to visualize the dummy source using the imager assembly, enabling source quality assurance measurements relative to the dummy source. In some embodiments, the scintillator is transparent to visible light, allowing the dummy source to be visualized employing the same channel as the active radiation source.

In another aspect, the disclosure can be used to perform quality assurance on clinical consumables. Commercially available clinical brachytherapy needles or applicators can be inserted into the acquisition unit to evaluate the clinical quality and/or manufacturing integrity of the manufactured needle or applicator batch. In some embodiments, the acquisition unit has an insertable bracket to directly load commercially available clinical brachytherapy needles or applicators. The brackets may accommodate more than one needle or applicator to allow simultaneous quality assurance on multiple needles or applicators. In one aspect, the proposed embodiment can measure the relative positional accuracy of the source in the manufactured needle/applicator. In another aspect, the proposed embodiment can measure trajectory of the radiation source as it passes through the needle/applicator to determine its manufacturing conformity.

In some embodiments, radiation sources or applicators are placed on the acquisition unit's exterior or interior. An explicit source placement system may or may not be used in tandem with a mount. In one aspect, the proposed embodiment measures the radioactivity, spatial positioning and/or dwell time of radioactive seeds mounted to the acquisition unit. In another aspect, the proposed embodiment tracks the dwell position, dwell time, and/or path line of the radioactive seed traveling through a brachytherapy applicator. In another aspect, the proposed embodiment is used for monitoring and/or measuring of radiation source dwell position, dwell time, and/or radioactivity within the patient. In another aspect, the proposed embodiment is used for measuring position and/or radioactivity of single sources or a cluster of sources employed in low-dose radiotherapy application.

In an embodiment, the acquisition unit performs quality assurance for an electronic brachytherapy system, where a point x-ray emitting source is employed instead of a radiation source. In another embodiment, the acquisition unit could also perform quality assurance for static and dynamic intensity modulated brachytherapy sources.

Some embodiments of the brachytherapy quality assurance system may perform patient quality assurance and post-delivery quality assurance by confirming the various dwell position and dwell time parameters delivered by the afterloader and comparing them to the patient treatment plan. Patient quality assurance is performed before or after the treatment in which the overall estimated radiation dose to the patient, including spatial information, is calculated and compared to the pre-treatment patient treatment plan. Post-delivery quality assurance confirms if the afterloader system delivered the correct parameters (dwell position, dwell time) after the patient treatment is completed. In some embodiments, this includes patient dose calculation which may or may not be based on prior acquired radiological images of the patient, which may or may not include specific patient tissue information. In some embodiments, the acquisition unit has multiple source placement systems incorporated to allow individual connection with multiple brachytherapy delivery system channels. When performing patient quality assurance, the system may verify that the treatment the patient received was what it was supposed to be and in accordance with acceptable processes and procedures. The system may also simply check if the positions and times were correct, or the system can import the positions/times into computed tomography or other radiological images and recalculate the dose completely.

Some embodiments of the brachytherapy quality assurance system include automatically deploying acquired camera data and processed numerical data to external software for storage and analysis, which could be either installed on a local machine or deployed to a cloud server for online management. The system may convert the data to be directly read in, or output to a data file to be read in by the software.

The application of the methods, systems, and devices disclosed herein may also be used in pre-clinical settings or in veterinary brachytherapy clinics.

Implementations of the brachytherapy quality assurance system embodiments are shown in the following sections. The designs are not limited to the described embodiments, but generally include variations that use scintillators, imagers, and needles embedded in a compact single unit.

For the purposes of promoting an understanding of the principles in accordance with the disclosure, reference will now be made to the embodiments illustrated in the drawings, and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Referring now to the figures, FIG. 1 is a schematic diagram of a system 100 for detecting and locating radiation emissions. The system 100 may include an optical assembly, semiconductor detector, or another platform capable of detection ionizing radiation sources. The example system 100 illustrated in FIG. 1 includes an imager assembly 102 that includes a camera 104 and a lens 106. The system 100 includes a scintillator 108, which may specifically include a scintillation crystal. The imager assembly 102 may include an optical assembly, one or more semiconductor detectors, or other platforms for acquiring ionizing radiation sources.

In the embodiment illustrated in FIG. 1, the radiation sources 110 may be permanently or removably secured directly to the scintillator 108. In some cases, the radiation sources 110 may be adhered to the scintillator 108 with tape or some other adhesive. In some applications, the radiation sources 110 may include a grouping of 20-50 small radiation sources implanted into a mold, and in this case, it can be important to ensure the radiation sources 110 are secured in the correct location relative to the scintillator 108 and the imager assembly 102.

The camera 104 captures images of the scintillator 108 and/or surrounding area. The camera 104 comprises an image sensor with a pixel array. The pixel array senses reflected electromagnetic radiation from objects within a scene and further senses electromagnetic radiation emitted by the scintillator 108. The scintillator 108 will glow when exposed to ionizing radiation. In FIG. 1, the scintillator 108 is glowing at three glowing regions 111 in response to emissions of ionizing radiation emitted by the three radiation sources 110. The camera 104 captures image data, and the image data is analyzed to identify the coordinates of the radiation sources 110 and the emitted radiation based on the locations of the glowing regions 111 on the scintillator.

The camera 104 includes one or more image sensors for capturing imaging data. The image sensors may include a filtered pixel array comprising red, green, and blue-sensitive filters for capturing red, green, and blue image data. The image sensors may include a monochromatic pixel array that is sensitive to any wavelength of electromagnetic radiation. The camera 104 captures one or more images of the scintillator 108 to identify the location of radiation passing through the scintillator 108. The images captured by the camera 104 may be fed to an image processing pipeline configured to assess the image data and determine the location of the radiation based on the image data.

The camera 104 may include a stereo pair of image sensors. The data output by the stereo pair of image sensors may be processed to generate a three-dimensional reconstruction of a scene and/or a three-dimensional localization of points within the image data. The camera 104 may include one or more digital cameras.

The camera 104 may include a bandpass filter. The bandpass filter passes an emission band of emission from the scintillator 108. The bandpass filter may be located in front of the image sensor such that electromagnetic radiation is filtered through the bandpass filter before being sensed by the pixel array of the image sensor.

The image data captured by the camera 104 may be stored and retrieved at a future time to review treatment delivery. The image data may be automatically offloaded to cloud-based storage for later retrieval.

The camera 104 and the radiation sources 110 may be synchronized such that the image sensor senses electromagnetic radiation at certain times depending on the emissions of energy by the radiation sources 110. This synchronization may be performed based on the internal clock for the camera 104 and/or an associated processor. This enables the acquisition of electromagnetic radiation only during a specified period of time. The image sensor may be actuated to sense electromagnetic radiation only when the radiation sources 110 are emitting energy and/or after the radiation sources 110 have ceased emitting energy.

The scintillator 108 is constructed of a material that exhibits scintillation, or the property of luminescence, when excited by ionizing radiation. Luminescent materials absorb energy and scintillate (i.e., re-emit the absorbed energy in the form of light) when struck by an incoming particle. The scintillator 108 may include an organic crystal, an organic liquid, a scintillating material suspended in a polymer matrix, an inorganic crystal, a gas, a glass, or another suitable scintillating material. The scintillator 108 may include a scintillating sheet disposed on a surface closely located to a radioactive seed. The scintillator 108 may specifically include a powder mixed with silicone, wherein the powder comprises the phosphor referred to as GdO2S:Tb or the phosphor referred to as GdO2S:Eu.

The scintillator 108 is located near the radiation sources 110, and in some cases, the scintillator 108 may make physical contact with the radiation sources 110. The scintillator 108 glows when exposed to ionizing radiation emitted by the radiation sources 110. The scintillator exhibits a glowing region on its surface when the scintillator 108 is exposed to a radioactive seed that passes underneath the scintillator 108. The image sensor of the camera 104 captures images of the scintillator 108 when the scintillator is glowing to identify the locations of radiation emissions.

The radiation sources 110 may be associated with and actuated by an external system, such as a brachytherapy or X-Ray system. The radiation sources 110 may include high-dose rate (HDR) brachytherapy radiation sources that may be inserted into a patient to target specific regions within the patient's body. The radiation sources 110 may include needles associated with an HDR brachytherapy system, wherein the needles are inserted into a patient's tissue and are attached to tubes that will deliver radiation through the needle. The radiation sources 110 may include micro X-Ray sources for point-source X-Ray applications. The radiation sources 110 may include any suitable sources of radiation for medical and non-medical applications. The radiation sources 110 may include high-dose, mid-dose, or low-dose brachytherapy seeds. The radiation sources 110 may provide a single radioactive seed or a cluster of radioactive seeds.

The systems described herein may further include a display for displaying images captured the image sensor in real-time. The systems described herein may include one or more processors for executing instructions and may specifically include one or more processors for executing an image processing algorithm for assessing the image data captured by the image sensor in real-time. The one or more processors and display enable a machine operator to perform real-time assessment of treatment delivery. Additionally, such data can be stored on recordable media for alter review.

FIG. 2 is a schematic diagram of a system 200 for detecting the coordinates and emissions of one or more radiation sources. The system 200 includes the radiation detection components illustrated in FIG. 1, including the imager assembly 102, the camera 104, the lens 106, and the scintillator 108. The system 200 further includes an enclosure 212 for protecting the imager assembly 102 from environmental light sources. The interior space of the enclosure 212 remains a light-deficient environment to improve the accuracy of the sensor readings captured by the imager assembly 102. The system 200 includes an x-position channel 214 configured as a single placement system for sensing x-positional information. The system 200 further includes an absolute position marker 216 for tracing absolution position.

The enclosure 212 protects the imager assembly 102 and scintillator 108 from environmental and ambient light sources. The enclosure 212 may be light-tight to ensure that the imager assembly 102 is disposed within a light-deficient environment. The enclosure 212 may be constructed of a rigid material to further protect the internal components from damage. In an implementation, the imager assembly 102 is mounted to the enclosure 212.

The x-position channel 214 provides a pathway for emissions of radiation. The x-position channel 214 may include a hollow tube connected to a radiation source 110 such that the radiation source 110 emits radiation directly into the interior cavity of the hollow tube. The absolute position marker 216 is disposed at the distal end (distal relative to the radiation source 110) of the x-position channel 214. The length of the x-position channel 214 from the proximal end (where the x-position channel 214 is connected to a radiation source 110) to the distal end (wherein the x-position channel 214 terminates at the absolute position marker 216) is a known quantity. The length of the x-position channel 214 is used to determine the coordinates of radiation relative to the absolute position marker 216 and relative to the coordinate system of the imager assembly 102. The absolute position marker 216 may be located at any position on the x-position channel 214.

The absolute position marker 216 is a physical marker that enables the system 200 to identify where the physical source is located within the x-position channel 214. The absolute position marker 216 lines up the coordinate system of the x-position channel 214 with the coordinate system of the imager assembly 102. The absolute position marker 216 may include a light source, such as an LED light source, that can be actuated to identify the location of the absolute position marker 216.

In the implementation illustrated in FIG. 2, the system 200 may be connected to a single afterloader channel of a brachytherapy system. The single afterloader channel may be coupled to the x-position channel 214 by way a radiation coupler.

Figure 3:
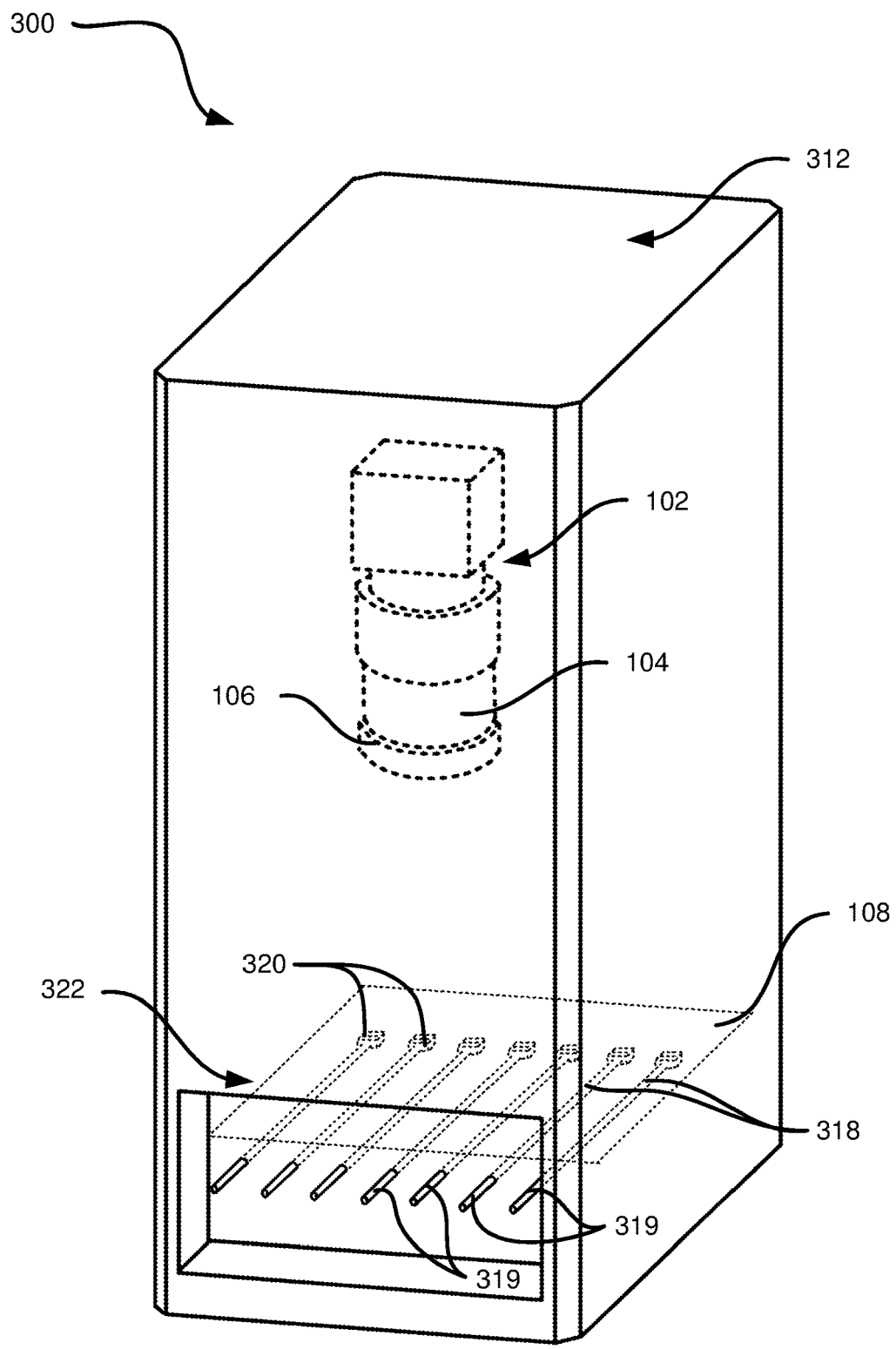
FIG. 3 is a schematic diagram of a system for measuring and tracking energy emitted by a radiation source, wherein the system includes a multi-channel placement system.

FIG. 3 is a schematic diagram of a system 300 for detecting the coordinates and emissions of one or more radiation sources. The system 300 includes a multi-channel placement assembly for detecting the coordinates of radiation emissions. The system 300 includes an enclosure 312 for protecting the imager assembly 102 from environmental and ambient light sources. The system 300 includes an imager assembly 102 including a camera 104 and lens 106, which may be similar to the imager assembly illustrated in connection with FIG. 1. The system 300 includes a scintillator 108 for visualizing the one or more radiation sources.

The system 300 further includes a multi-channel placement assembly 322. The multi-channel placement assembly 322 includes a plurality of positional channels 318 which may each optionally include an absolute position marker 320 as illustrated in FIG. 3. The positional channels 318 are similar to the x-position channel 214 illustrated in FIG. 2 in terms of structure and function. Each of the positional channels 318 includes a proximal end wherein the positional channel 318 can connect to a radiation source 110, and further includes a distal end wherein the positional channel 318 terminates at an absolute position marker 320. The positional channels 318 may include hollow tubes or another means for guiding the emission of radiation from the radiation source 110 to the desired destination.

In an embodiment, each of the positional channels 318 includes a radiation coupler 319 at the proximal end. The radiation coupler 319 connects the positional channel 318 to a radiation source 110 via a brachytherapy transfer guide tube or equivalent system such that the radiation source 110 emits radiation into the positional channel 318. The length of the positional channel 318 from the radiation coupler 319 to the absolute position marker 320 is a known quantity. This known quantity is used to sync the location of the multi-channel placement assembly 322 with the coordinate system of the imager assembly 102.

The absolute position markers 320 may be similar in structure and function to the absolute position marker 216 described in connection with FIG. 2. The absolute position markers 320 are physical markers that enable the system 300 to identify where the radiation is located within the positional channels 318. The absolute position markers 320 line up the coordinate system of the multi-channel placement assembly 322 with the coordinate system of the imager assembly 102. The absolute position markers 320 may each include a light source, such as an LED light source, that can be actuated to identify the locations of the absolute position markers 320.

In the implementation illustrated in FIG. 3, the system 300 may be connected to multiple afterloader channels of a brachytherapy system. Each of the multiple afterloader channels may be coupled to a single position channel 318 by way of a radiation coupler 319 and a brachytherapy transfer guide tube or other equivalent system. The system 300 may be implemented to evaluate the health, performance, and condition of the afterloader motor and encoding system, and/or the afterloader timing system.

Figure 4:
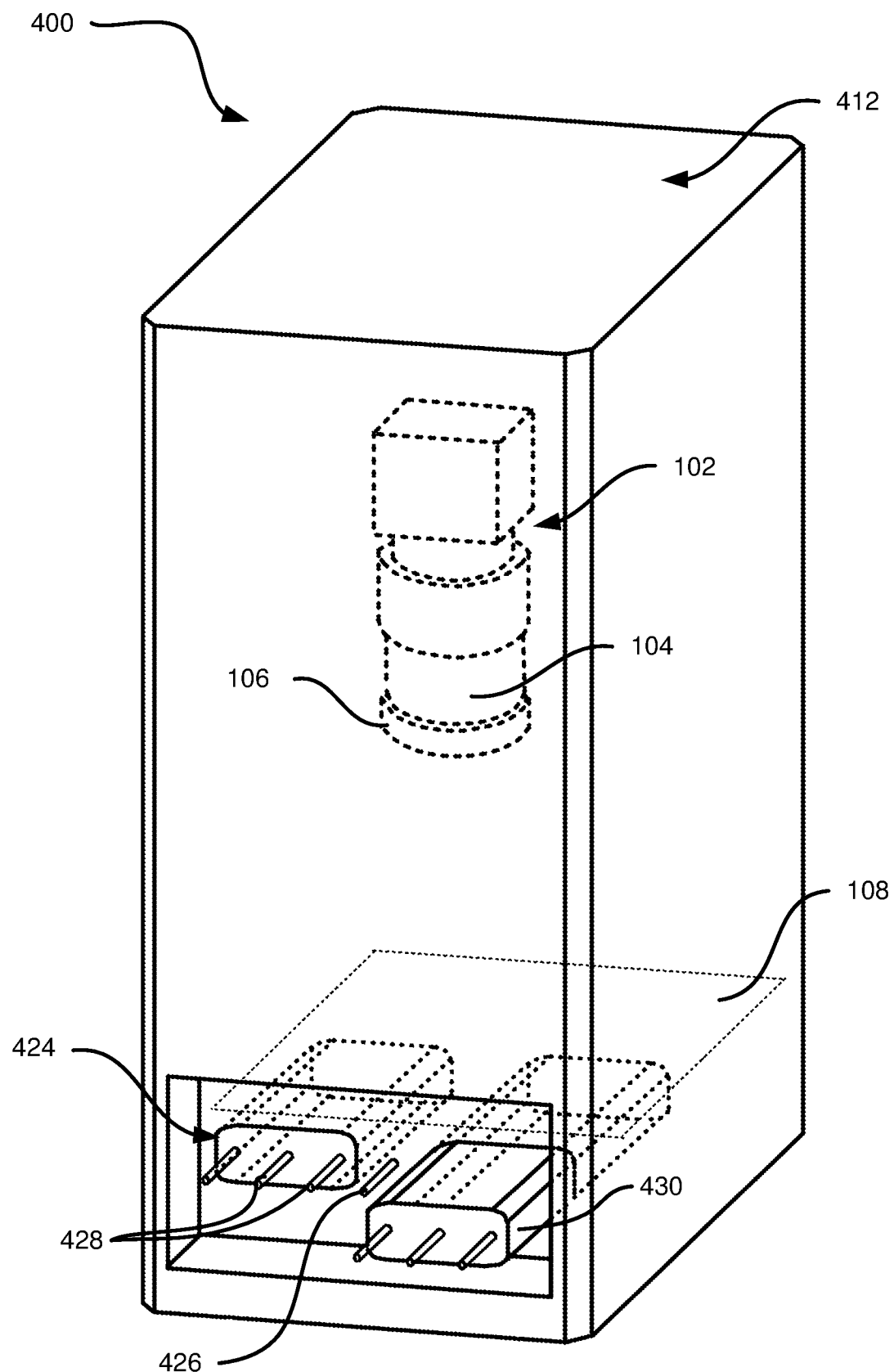
FIG. 4 is a schematic diagram of a system for measuring and tracking energy emitted by a radiation source, wherein the system includes brackets for mounting one or more needles or applicators configured for supplying radiation to an intended region.

FIG. 4 is a schematic diagram of a system 400 for detecting the coordinates and emissions of one or more radiation sources. The system 400 includes brackets for mounting an application or clinical needle for administering radiation to a patient. The system 400 includes an enclosure 412 to protect the internal components of the system 400 from environmental and ambient light sources. The system 400 includes an imager assembly 102 including a camera 104 and a lens 106, which may be similar to the imager assembly 102 illustrated in FIG. 1. The system 400 includes a scintillator 108 for visualizing the one or more radiation sources.

The system 400 further includes a placement assembly 424 for connecting the system 400 to a brachytherapy system for delivering radiation to internal tissues of a patient. The placement assembly 424 may include a placement 426 for securing and connecting the system 400 to a brachytherapy system such that the system 400 can be implemented to identify the absolute coordinates and emissions of the one or more radiation sources of the brachytherapy system. The system 400 thereby serves to determine if a batch of needles 428 meet the functional clinical requirements to be employed in patient brachytherapy. The placement assembly 424 includes one or more needles 428, which may be constructed of plastic or metal, and may be supplied by an administrator of the brachytherapy. Needles 428 are consumables and may be constructed by an outside vendor for administering patient brachytherapy. The placement assembly 424 includes a removable bracket 430 for mounting the needles 428 securely inside the system 400. The system 400 is capable of determining whether the needles 428 are functioning within clinical specification when providing brachytherapy.

Figure 5:
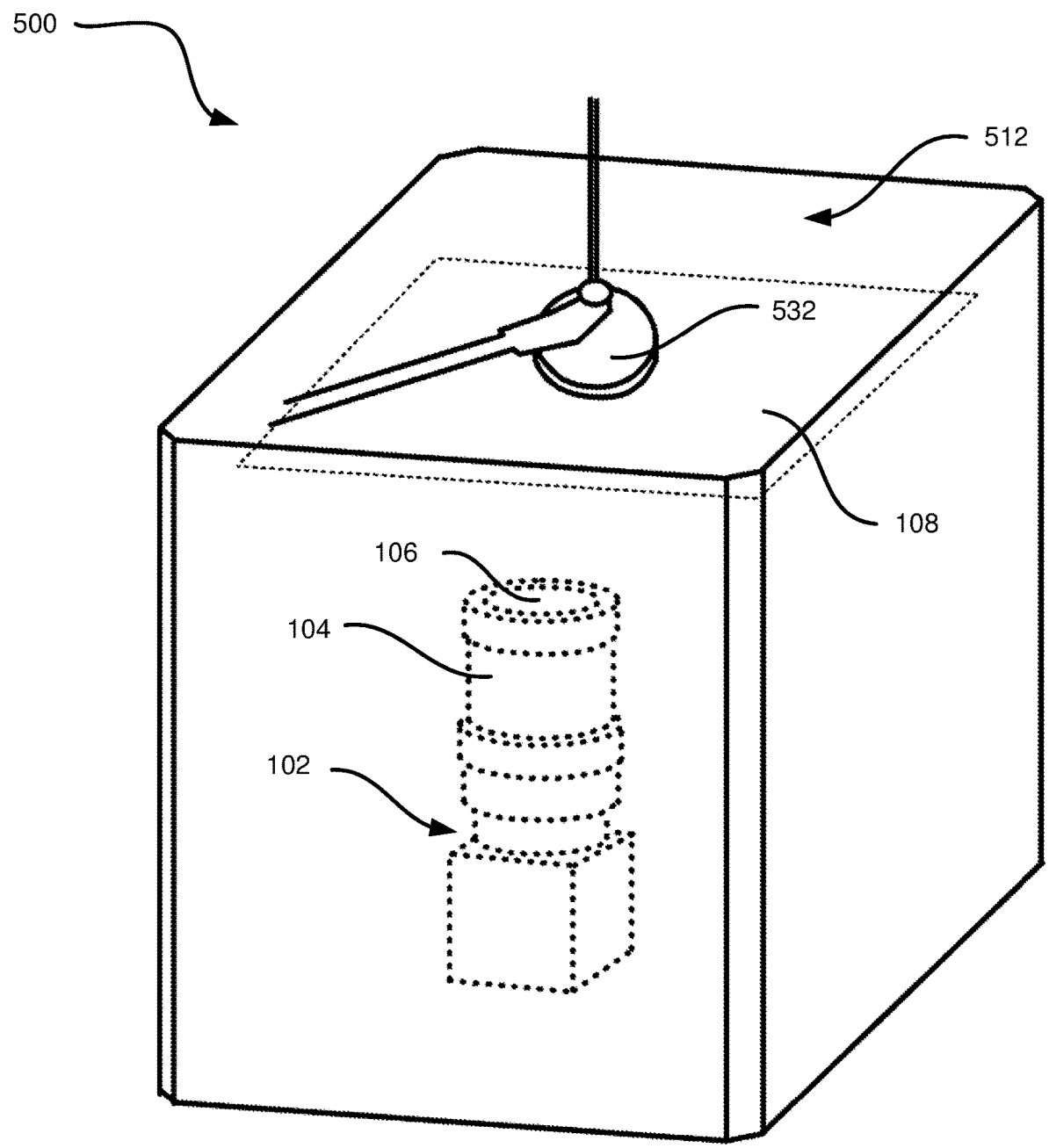
FIG. 5 is a schematic diagram of a system for measuring and tracking energy emitted by a radiation source, wherein the system is configured for mounting to a surface of a radiation system.

FIG. 5 is a schematic diagram of a system 500 for detecting the coordinates and emissions of one or more radiation sources. The system 500 can be mounted on the surface of a brachytherapy applicator. The system 500 includes an enclosure 512 for protecting the internal components of the system 500 from environmental and ambient light sources. The system 500 includes a scintillator 108 for visualizing the one or more radiation sources. The system 500 includes an imager assembly 102 including an image sensor 104 and a lens 106, wherein the imager assembly 102 may be similar to that illustrated in FIG. 1.

FIG. 5 illustrates an example wherein the system 500 is placed on the surface of a brachytherapy applicator on top of a scintillator directly mounted to the surfaced of the enclosure 512 In an alternative implementation, a standalone radiation source may be used.

The systems described herein may be connected to consumable catheters or applicators for a brachytherapy system or other system for delivering radiation. The systems described herein can be implemented to evaluate the manufacturing integrity of consumable catheters or applicators, including, for example, the straightness of source travel along the length of the catheter or application; the relative position accuracy within the catheter or applicator; and the ease of travel, measured by consistent velocity, through the catheter or applicator.

The systems described herein may be implemented to evaluate the health, performance, and condition of numerous components of a brachytherapy system. For example, the systems can be implemented to evaluate the health, performance, and condition of the afterloader motor, the encoding system, and the afterloader timing system.

The image processing calculates determined herein may be compared with treatment planning data to determine the efficacy of treatment delivery. This may include corresponding with treatment planning software of a radiation system to determine whether the radiation was supplied in the correct regions for the correct amount of time, and whether the correct amount of total radiation energy was supplied. The systems described herein are configured to determine whether the radiation was supplied to the correct location based on patient anatomical landmarks that are determined during data processing. This may be compared with relative locations of corresponding elements in a treatment plan.

The image processing data calculated herein may be presented with a deviation tolerance. The deviation tolerance may indicate a deviation threshold for supplying the intended amount of radiation, the intended time for delivering radiation, and the intended location for delivering radiation. The systems described herein can determine whether the actual amount, location, and time of radiation delivered is consistent with the prescribed treatment plan within a tolerance threshold. The systems can further determine the efficacy of the radiation source, and whether the radiation source is operating as intended.

Figure 6:
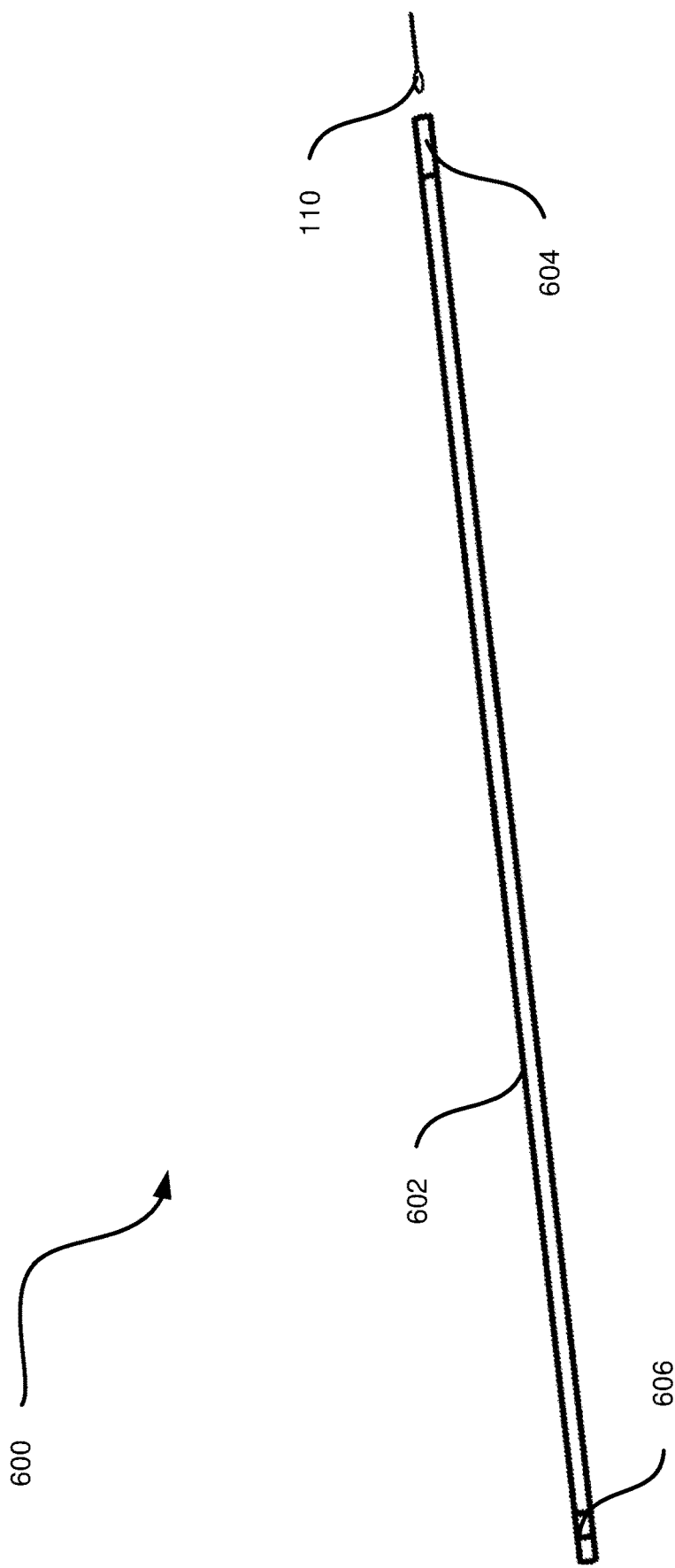

FIG. 6 is a schematic diagram of a placement assembly 600. The placement assembly 600 comprises components for measuring absolute position and for syncing the coordinates of a positioning system with the coordinates of an imager assembly 102 as described herein. It will be appreciated that the dimensions and shape of the placement assembly 600 are subject to change depending on radiation source dimensions. The placement assembly 600 includes a positional channel 602, which may include a hollow tube for guiding radiation as described herein. The placement assembly 600 includes a radiation coupler 604 for coupling the positional channel 602 to a radiation source 110 such that the radiation source can emit radiation into the positional channel 602. The placement assembly 600 includes an absolute position marker 606 for tracking absolute position of the radiation source 110.

The positional channel 602 may include a hollow tube or pipe in which radiation source 110 can travel into. The positional channel 602 may be transparent or opaque depending on the implementation and the specific needs of the application. The positional channel 602 may serve as a transfer guide tube for connecting to brachytherapy needles.

The absolute position marker 606 includes a fiducial marking such as dots, lines, hashing, and so forth. The absolute position marker 606 is located at the distal end of the positional channel 602 (wherein the proximal end is located at the radiation source 110), and the distance of the absolute position marker 606 to the radiation source 110 is a known quantity. The fiducial marking may be located at any position on the positional channel 602. Similarly, the absolute position marker 606 may be located at any position on the positional channel 602.

Figure 7:
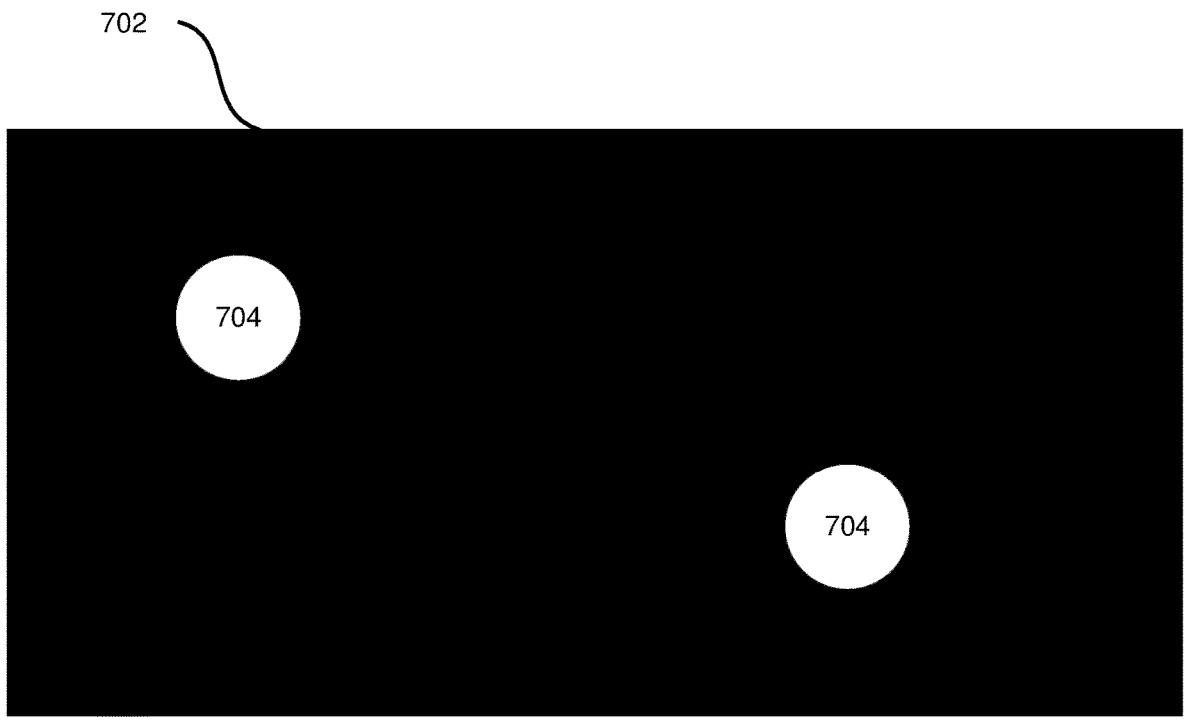
FIG. 7 illustrates an example image frame captured by an image sensor, wherein the image frame includes a plurality of regions of interest.

FIG. 7 is a schematic diagram of an example image frame 702 captured by the image sensor. The image frame 702 may be captured in an implementation wherein the imager assembly 102 and the scintillator 108 are disposed within an enclosure such that the interior space of the enclosure is entirely light-deficient. In this embodiment, the image sensor will capture the absence of electromagnetic radiation (darkness), and the only electromagnetic radiation captured by the image sensor will include the energy emitted by the radiation source that is scintillated by the scintillator 108.

The image frame 702 is captured by the image sensor which faces directly toward the scintillator 108. The image frame 702 may include a portion of the scintillator 108, the entirety of the scintillator 108, or the scintillator 108 and additional background surrounding the scintillator 108. In the example illustrated in FIG. 7, the image frame 702 depicts two scintillating regions 704. The scintillating regions indicate regions wherein the scintillator 108 is scintillating energy (i.e., re-emitting absorbed energy, wherein the energy is originally emitted by the radiation source 110). If the enclosure is successfully light-deficient, then the scintillating regions will constitute the only regions of electromagnetic radiation that can be sensed by the image sensor. The region surrounding the scintillating regions 704 will indicate the absence of electromagnetic radiation (darkness).

The image frame 702 depicts a stark contrast between the scintillating regions 704 and the surrounding regions of darkness. However, it should be appreciated that the scintillating regions 704 will often appear as gradient regions, wherein a center-point of the scintillating region 704 comprises the greatest amount of electromagnetic radiation, and the intensity of the electromagnetic radiation decreases with distance from the center-point. In this case, the brightness intensity of the pixels on the pixel array of the image sensor will also have a gradient intensity. The center-point pixels of the scintillating region 704 will comprise the greatest brightness, and the brightness of the surrounding pixels will decrease.

The systems described herein include one or more processors for executing an image processing algorithm. The image processing algorithm is executed on the image frames captured by the image sensor and may specifically be executed on a plurality of sequentially captured image frames. The sequentially-captured image frames may be captured at a high frame rate depending on the implementation. The image processing algorithm is implemented to calculate, for example, the intensity of the energy emitted by the radiation source 110. The intensity of the energy is calculated based on the amount of electromagnetic radiation sensed by the pixels of the image sensor, which is reflected by the brightness of each pixel in the image frame. The image processing algorithm is additionally implemented to calculate, for example, the velocity of the movement of the energy emitted by the radiation source, the total intensity of energy provided by the radiation source, the total intensity of energy provided by one emitter of the radiation source, and the travel pathway of the energy emitted by the radiation source. The determinations made by the image processing algorithm can be compared with an intended treatment program to determine whether a patient received the desired intensity of energy in the correct regions.

Figure 8:
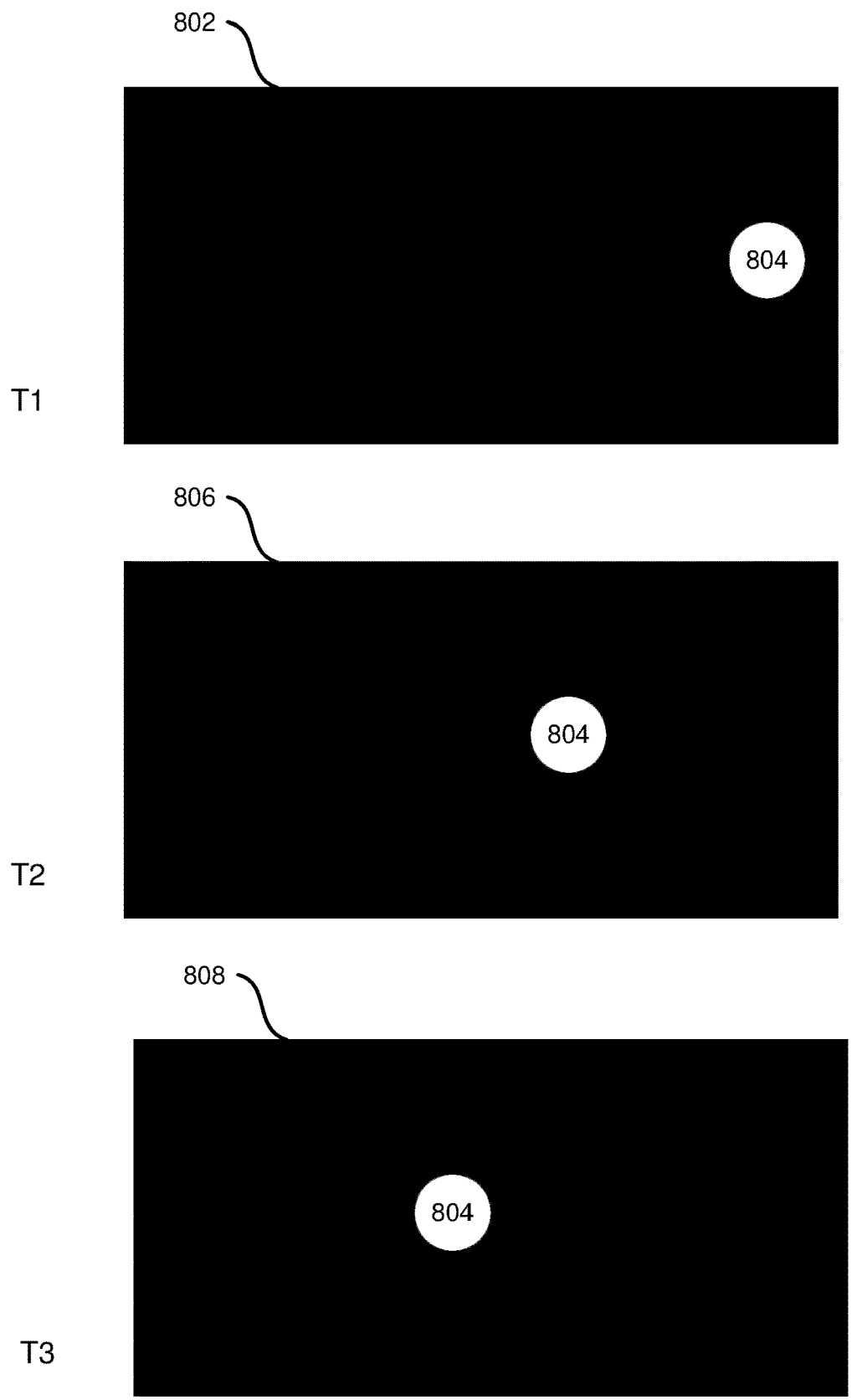
FIG. 8 illustrates an example plurality of sequential image frames captured by an image sensor, wherein the plurality of sequential image frames depict the movement of a region of interest over time.

FIG. 8 illustrates a plurality of sequential image frames captured by the image sensor. The sequential image frames include a first image frame 802 captured at T1, a second image frame 806 captured at T2, and a third image frame 808 captured at T3. Each of the sequential image frames comprises a depiction of the same scintillating region 804. The scintillating region 804 moves across the scintillator 108 over time, and the plurality of sequential image frames depict the movement of the scintillating region 804 over time. The image processing algorithm can be executed to determine the velocity of the energy emitted by the radiation source based on the movement of the scintillating region 804 across the sequential image frames.

Figure 9:
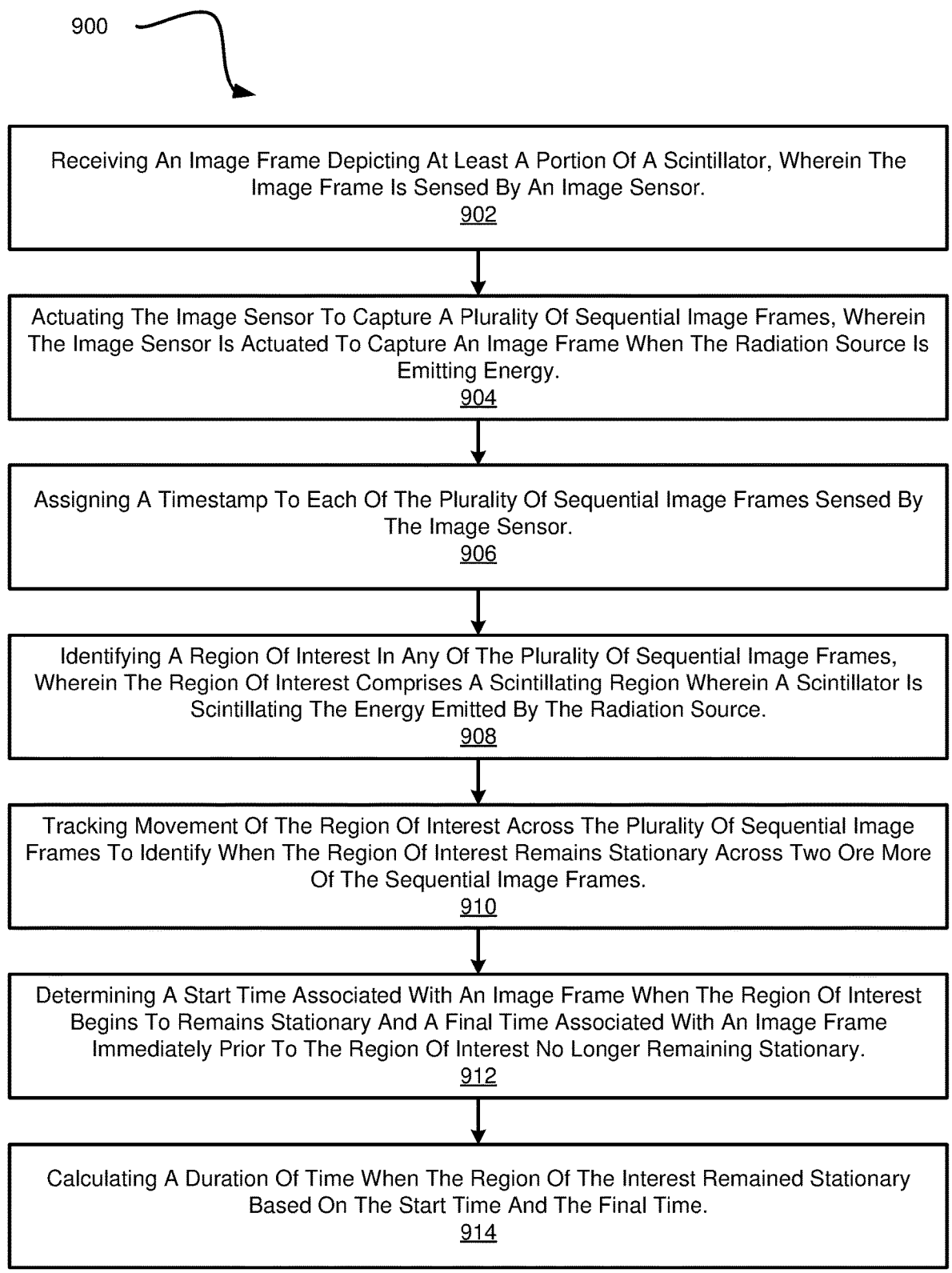
FIG. 9 is a schematic flow chart diagram of a method for calculating a stationary time period for a region of interest in an image frame.

FIG. 9 is a schematic flow chart diagram of a method 900 for stationary time period for a region of interest in an image frame or plurality of frames. The method may be performed by one or more processors configured to execute instructions stored in non-transitory computer readable storage media. The one or more processors are in communication with the imager assembly 102 and camera 104 described herein. The method 900 may be executed by processing resources on a server in communication with a network. The method 900 may be executed by processing resources local to the camera 104 and/or local to a computing device in communication with the camera 104.

The method 900 begins at 902 with receiving an image frame that depicts at least a portion of a scintillator 108. The image frame is sensed by an image sensor of the camera 104 of the imager assembly 102. The image frame may comprise an indication that the scintillator 108 is scintillating from absorbing and re-emitting energy emitted by the radiation source 110. The radiation source 110 may be moved underneath the scintillator 108 using the afterloader control. The radiation source 110 may include one or more radiation sources associated with a brachytherapy system. The radiation source 110 may include a single afterloader channel of a brachytherapy system, multiple afterloader channels of a brachytherapy system, a micro X-Ray emitter, an X-Ray emitter, and so forth. The radiation source 110 may provide the energy through a needle, catheter or other applicator for administering the radiation to a patient.

The method 900 continues with actuating at 904 the image sensor to capture a plurality of sequential image frames. The image sensor is actuated to capture the plurality of sequential image frames when the radiation source is actively emitting energy. In an alternative implementation, the image sensor is actuated to capture the plurality of sequential image frames after the radiation source has emitted the energy. The image sensor may be actuated at 904 to capture a portion of the plurality of sequential image frames when the radiation source is actively emitted the energy, and to capture a different portion of the plurality of sequential image frames after the radiation source has ceased emitting the energy. The plurality of sequential image frames may be captured in quick succession at a high frame rate. The frame rate of the image sensor may be, for example, 5-200 frames per second.

The method 900 continues with assigning at 906 a timestamp to each of the plurality of sequential image frames sensed by the image sensor. The timestamp may be determined from the time of acquisition of an individual frame using the clock associated with the camera 104 or an attached computing processor. In an implementation, the image sensor is not formally synchronized with the radiation source. The camera 104 may remain on and ready such that the image sensor continuously detects a signal from the scintillator 108 in real-time and measures the intensity, the location of the center of the scintillating region, and the amount of time. The time data is calculated based on the camera 104 and/or computer internal clock.

The method 900 continues with identifying at 908 a region of interest in any of the plurality of sequential image frames. The region of interest may comprise a scintillating region 704, 804. The scintillating region may include a "glowing" region where the scintillator 108 is scintillating the energy that was emitted by the radiation source 110 and absorbed by the scintillator 108. The scintillating region 704, 804 is a luminescent region on the scintillator 108. The region of interest may be identified at 908 by calculating a signal to noise ratio, contrast-to-noise ratio for the image frame and/or pixel intensity values for the image frame. In an implementation, the image sensor and the scintillator 108 are disposed within a light-tight enclosure such that the scintillation emitted by the scintillator 108 represents the only electromagnetic radiation sensed by the image sensor. In this implementation, the image frames sensed by the image sensor may include dark regions (indicating the absence of electromagnetic radiation) and regions with bright pixel intensity, indicating regions where the scintillator 108 is scintillating the energy emitted by the radiation source.

The method 900 continues with tracking at 910 the movement of the region of interest across the plurality of sequential image frames to identify when the region of interest remains stationary across two or more of the sequential image frames. The region of interest remains stationary if the region of interest remains stationary within a threshold degree, and it should be appreciated that the region of interest may exhibit some movement across sequential image frames and still be classified as remaining stationary. When the region of interest remains stationary, this may indicate that the radioactive seed emitted by the radiation source 110 is remaining stationary to radiate a certain position. This may be done intentionally during a radiation procedure such as a brachytherapy procedure.

The method 900 continues with determining at 912 a start time associated with an image frame, wherein the start time is the timestamp associated with a first image frame when the region of interest begins to remain stationary. The determining at 912 further includes determining a final time associated with the region of interest ceasing to remain stationary. The final time is the timestamp associated with an image frame immediately prior to the region of interest no longer remaining stationary. This step may include identifying the first image frame when the region of interest begins to move, and then selecting the timestamp for the image frame immediately prior to that first image.

The method 900 continues with calculating at 914 a duration of time when the region of interest remained stationary based on the start time and the final time. This duration of time may be used to calculated how long the radioactive seed remained stationary at a certain location. This can further be used to determine the total amount of radiation energy that was supplied to the certain location when the radioactive seed remained stationary. These determinations can be compared with the desired treatment protocol to determine whether the treatment protocol was executed successfully and/or the radiation system is operating properly.

FIG. 10 is a schematic flow chart diagram of a method 1000 for identifying a geometric center of a region of interest in an image frame. The method 1000 may be performed by one or more processors configured to execute instructions stored in non-transitory computer readable storage media. The one or more processors are in communication with the imager assembly 102 and camera 104 described herein. The method 1000 may be executed by processing resources on a server in communication with a network. The method 1000 may be executed by processing resources local to the camera 104 and/or local to a computing device in communication with the camera 104.

The method 1000 begins with calculating at 1002 a contrast-to-noise ratio of an image frame and calculating pixel intensity values for a plurality of pixels in the image frame. The method 1000 continues with applying at 1004 an adaptive threshold to the histogram. A constant cutoff value is employed across the entire image frame to eliminate noise that might result in a false positive detection. The cutoff value is based on a histogram of pixels in the image, thresholding out all pixels below the maximum level of an image where no scintillation is present.

The method 1000 continues with extracting at 1006 contours of a region of interest in the image frame. The region of interest includes a scintillating region as described herein. The scintillating region includes a region wherein the scintillator is scintillating energy that was emitted by a radiation source and absorbed by the scintillator. The method 1000 continues with identifying at 1008 a geometric center of the region of interest. This can be employed using a peak finding algorithm, including but not limited to a two-gaussian across the spatial data.

Figure 11:
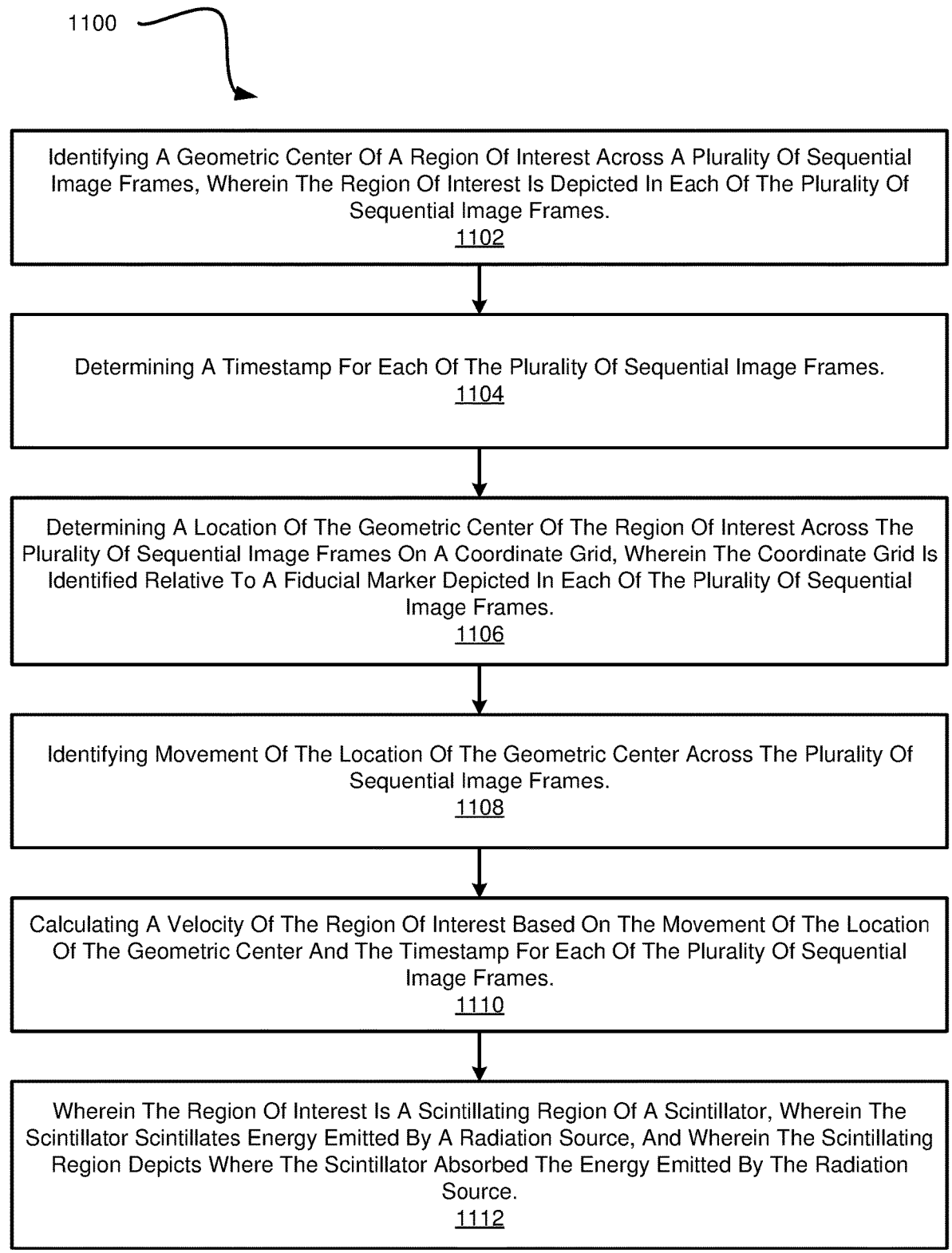
FIG. 11 is a schematic flow chart diagram of a method for calculating a velocity of energy emitted by a radiation source based on image data.

FIG. 11 is a schematic flow chart diagram of a method 1100 for calculating a velocity of energy emitted by a radiation source based on image data. The method 1100 may be performed by one or more processors configured to execute instructions stored in non-transitory computer readable storage media. The one or more processors are in communication with the imager assembly 102 and camera 104 described herein. The method 1100 may be executed by processing resources on a server in communication with a network. The method 1100 may be executed by processing resources local to the camera 104 and/or local to a computing device in communication with the camera 104.

The method 1100 begins with identifying at 1102 a geometric center of a region of interest across a plurality of sequential image frames, wherein the region of interest is depicted in each of the plurality of sequential image frames. The method 1100 continues with determining at 1104 a timestamp for each of the plurality of sequential image frames.

The method 1100 continues with determining at 1106 a location of the geometric center of the region of interest across the plurality of sequential image frames on a coordinate grid. The coordinate grid is identified relative to a fiducial marker depicted in each of the plurality of sequential image frames. The fiducial marker is printed on an absolute position marker as described herein (see, for example, 216, 320, 606). The position of the absolute position marker (and therefore, the position of the fiducial marker) may be determined by illuminating the absolute position marker with a light source and capturing an image frame of the scene when the light source is illuminated. As the coordinate system of the path of the radiation source 110 relative to the absolute position fiducial marker is a known quantity, the coordinate system of the camera system 102 can therefore be registered with it. The coordinate grid may be calibrated relative to the fiducial marker upon startup for the system. This calibration may occur prior to the radiation source emitting the energy and/or the image sensor capturing the plurality of sequential image frames.

The location of the region of interest (i.e., the location of the radioactive seed) may be compared with the prescribed position of the radioactive seed according to a brachytherapy afterloader system. Additionally, the time a region of interest (i.e., a radioactive seed) spends at a stationary position may be compared with the prescribed time according to the brachytherapy afterloader system.

The method 1100 continues with identifying at 1108 movement of the location of the geometric center across the plurality of sequential image frames. The movement of the location of the geometric center may be determined and calculated relative to the coordinate grid. As discussed herein, the coordinate grid for the image sensor is calibrated with the position of the absolute position marker. The movement of the region of interest is determined based on the region of interest moving across the coordinate grid. The image sensor and the scintillator 108 may remain stationary while the image sensor captures the plurality of sequential image frames. The energy emitted by the radiation source may move across the scintillator 108 over time (this may occur because the energy moves through a positioning channel as described herein). The movement of the scintillating region may be calculated in terms of the position of the scintillating region relative to a coordinate scale. The position of the coordinate scale may be calibrated relative to a fiducial marker located on an absolute position marker as described herein.

The method 1100 continues with calculating at 1110 a velocity of the region of interest based on the movement of the location of the geometric center and the timestamp for each of the plurality of sequential image frames. The method 1100 is such that the region of interest is a scintillating region of a scintillator (see 1112). The scintillator absorbs energy emitted by a radiation source and scintillates (i.e., re-emits) the energy to create a glowing region. This glowing region is referred to as the scintillating region.

Figure 12:
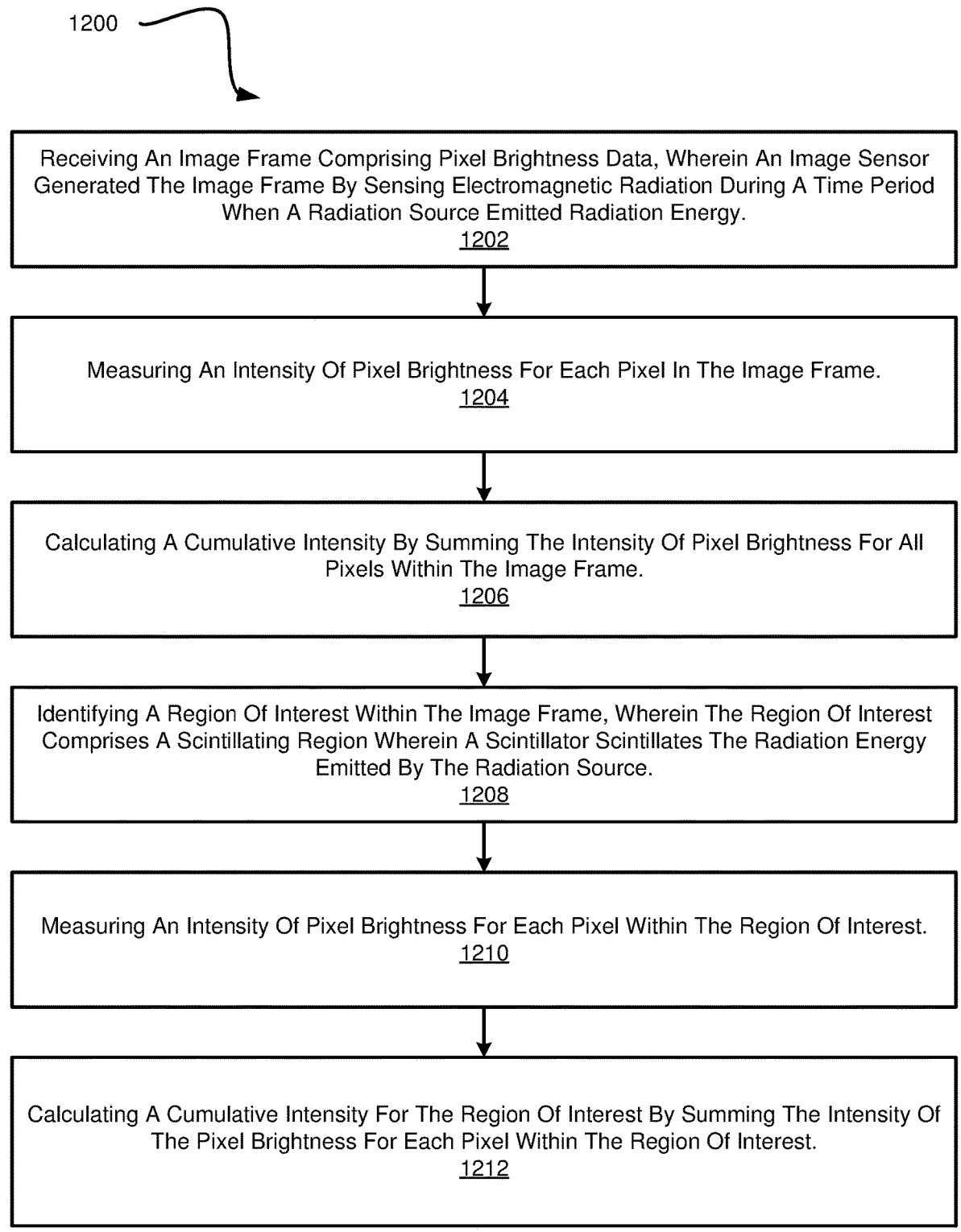
FIG. 12 is a schematic flow chart diagram of a method for calculating an intensity of an emission of energy by a radiation source.

FIG. 12 is a schematic flow chart diagram of a method 1200 for calculating an intensity of an emission of energy by a radiation source. The method 1200 may be performed by one or more processors configured to execute instructions stored in non-transitory computer readable storage media. The one or more processors are in communication with the imager assembly 102 and camera 104 described herein. The method 1200 may be executed by processing resources on a server in communication with a network. The method 1200 may be executed by processing resources local to the camera 104 and/or local to a computing device in communication with the camera 104.

The method 1200 begins with receiving at 1202 an image frame comprising pixel brightness data. The image frame is sensed by an image sensor. The image sensor generates the image frame by sensing electromagnetic radiation during a time period when a radiation source emits radiation energy and/or after the radiation source has emitted the radiation energy. The method 1200 continues with measuring at 1204 an intensity of pixel brightness for each pixel in the image frame. The method 1200 continues with calculating at 1206 a cumulative intensity by summing the intensity of pixel brightness for each pixel within the image frame.

In the case of supplying radiation to a patient with a brachytherapy or other procedure, the cumulative intensity of the pixel brightness is used to determine the cumulative intensity of the radioactivity emitted by the radiation source. This may be calculated as the "total dose" of radioactivity that is administered. This measurement may be compared with a known truth based on a decay curve of the radioactive source as referenced by the National Institute of Standards and Technology. The linearity of the total dose may be measured against the dwell time of the radiation source at a given location. The total time at a given position may be summed up to a single value of the procedure is interrupted. The total intensity at a given position may be summed up to a single value if the procedure is interrupted. The total dose at a given position may be summed up to a single value of the procedure is interrupted.

The method 1200 continues with identifying at 1208 a region of interest within the image frame. The region of interest comprises a scintillating region wherein a scintillator scintillates the radiation energy emitted by the radiation source. The method 1200 continues with measuring at 1210 an intensity of pixel brightness for each pixel within the region of interest. The method 1200 continues with calculating at 1212 a cumulative intensity for the region of interest by summing the intensity of the pixel brightness for each pixel within the region of interest.

Figure 13:
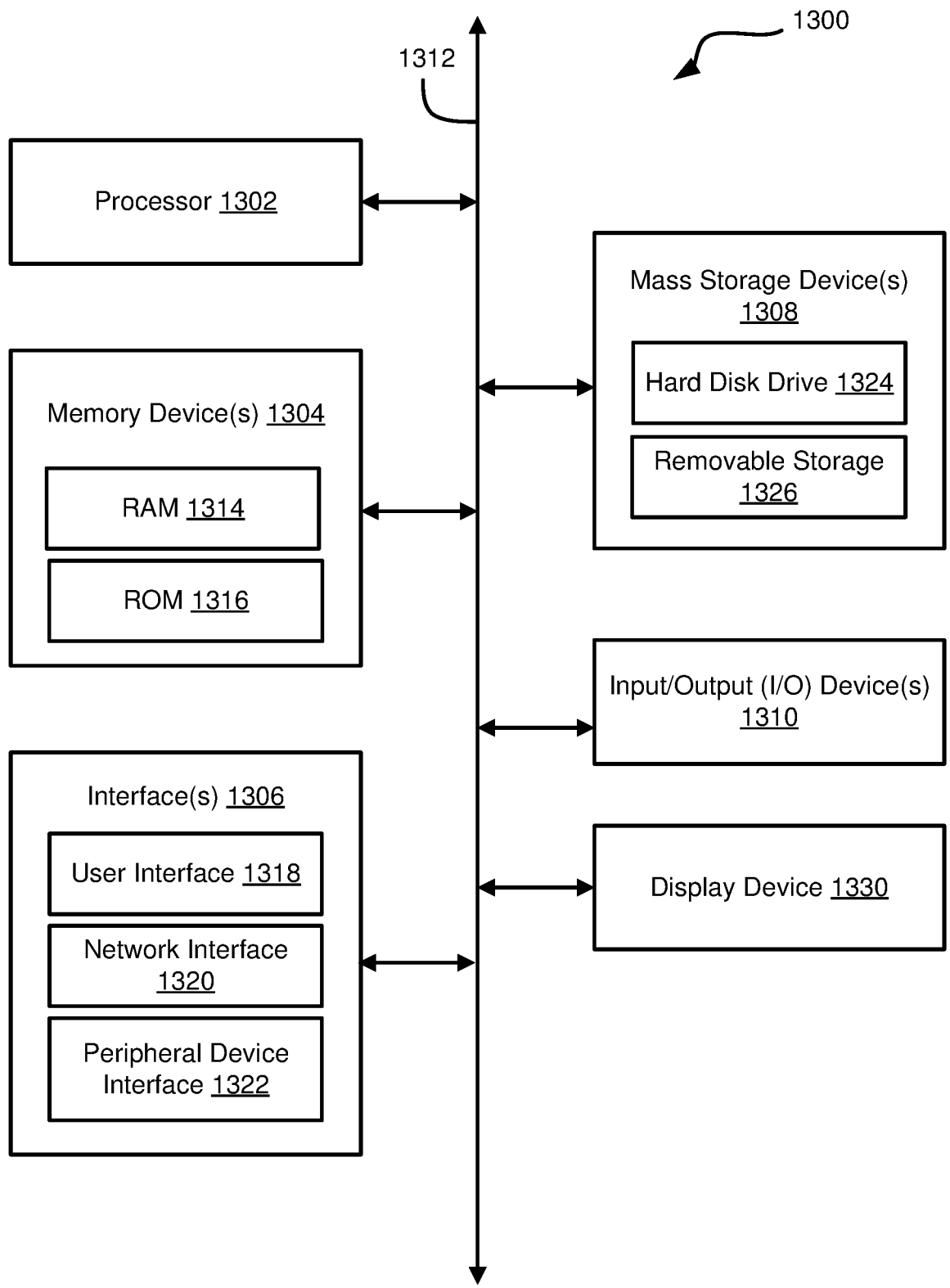
FIG. 13 is a schematic diagram illustrating components of an example computing device.

Referring now to FIG. 13, a block diagram of an example computing device 1300 is illustrated. Computing device 1300 may be used to perform various procedures, such as those discussed herein. Computing device 1300 can perform various monitoring functions as discussed herein, and can execute one or more application programs, such as the application programs or functionality described herein. Computing device 1300 can be any of a wide variety of computing devices, such as a desktop computer, in-dash computer, vehicle control system, a notebook computer, a server computer, a handheld computer, tablet computer and the like.

Computing device 1300 includes one or more processor(s) 1304, one or more memory device(s) 1304, one or more interface(s) 1306, one or more mass storage device(s) 1308, one or more Input/output (I/O) device(s) 1310, and a display device 1330 all of which are coupled to a bus 1312. Processor(s) 1304 include one or more processors or controllers that execute instructions stored in memory device(s) 1304 and/or mass storage device(s) 1308. Processor(s) 1304 may also include various types of computer-readable media, such as cache memory.

Memory device(s) 1304 include various computer-readable media, such as volatile memory (e.g., random access memory (RAM) 1314) and/or nonvolatile memory (e.g., read-only memory (ROM) 1316). Memory device(s) 1304 may also include rewritable ROM, such as Flash memory.

Mass storage device(s) 1308 include various computer readable media, such as magnetic tapes, magnetic disks, optical disks, solid-state memory (e.g., Flash memory), and so forth. As shown in FIG. 13, a particular mass storage device 1308 is a hard disk drive 1324. Various drives may also be included in mass storage device(s) 1308 to enable reading from and/or writing to the various computer readable media. Mass storage device(s) 1308 include removable media 1326 and/or non-removable media.

I/O device(s) 1310 include various devices that allow data and/or other information to be input to or retrieved from computing device 1300. Example I/O device(s) 1310 include cursor control devices, keyboards, keypads, microphones, monitors or other display devices, speakers, printers, network interface cards, modems, and the like.

Display device 1330 includes any type of device capable of displaying information to one or more users of computing device 1300. Examples of display device 1330 include a monitor, display terminal, video projection device, and the like.

Interface(s) 1306 include various interfaces that allow computing device 1300 to interact with other systems, devices, or computing environments. Example interface(s) 1306 may include any number of different network interfaces 1320, such as interfaces to local area networks (LANs), wide area networks (WANs), wireless networks, and the Internet. Other interface(s) include user interface 1318 and peripheral device interface 1322. The interface(s) 1306 may also include one or more user interface elements 1318. The interface(s) 1306 may also include one or more peripheral interfaces such as interfaces for printers, pointing devices (mice, track pad, or any suitable user interface now known to those of ordinary skill in the field, or later discovered), keyboards, and the like.

Bus 1312 allows processor(s) 1304, memory device(s) 1304, interface(s) 1306, mass storage device(s) 1308, and I/O device(s) 1310 to communicate with one another, as well as other devices or components coupled to bus 1312. Bus 1312 represents one or more of several types of bus structures, such as a system bus, PCI bus, IEEE bus, USB bus, and so forth.

For purposes of illustration, programs and other executable program components are shown herein as discrete blocks, such as block 202 for example, although it is understood that such programs and components may reside at various times in different storage components of computing device 1300 and are executed by processor(s) 1302. Alternatively, the systems and procedures described herein, including programs or other executable program components, can be implemented in hardware, or a combination of hardware, software, and/or firmware. For example, one or more application specific integrated circuits (ASICs) can be programmed to carry out one or more of the systems and procedures described herein.

EXAMPLES

The following examples pertain to further embodiments.

Example 1 is a system. The system includes an image sensor for sensing electromagnetic radiation and a scintillator, wherein the scintillator absorbs energy emitted by a radiation source and scintillates the absorbed energy. The system is such that the image sensor senses an image frame depicting at least a portion of the scintillator when the radiation source emits the energy, and wherein the image frame comprises an indication of where the energy is absorbed by the scintillator.

Example 2 is a system as in Example 1, further comprising an enclosure comprising an interior space, wherein the image sensor and the scintillator are disposed within the interior space of the enclosure, and wherein the enclosure prevents ambient light from reaching the image sensor or the scintillator such that the interior space is light-deficient.

Example 3 is a system as in any of Examples 1-2, further comprising an imager assembly comprising the image sensor and a lens, wherein the imager assembly is mounted to a wall of the enclosure, and wherein the imager assembly is disposed within the interior space of the enclosure.

Example 4 is a system as in any of Examples 1-3, further comprising a positional assembly, wherein the positional assembly comprises: a positional channel comprising a proximal end and a distal end, wherein the proximal end is nearer the radiation source or afterloader; and an absolute position marker disposed at the distal end of the positional channel.

Example 5 is a system as in any of Examples 1-4, wherein: the positional assembly further comprises a radiation coupler, wherein the radiation coupler is disposed at the proximal end of the positional channel for coupling the positional channel to the radiation source or afterloader; and the positional channel comprises a hollow tube for communicating the energy emitted by the radiation source.

Example 6 is a system as in any of Examples 1-5, wherein the scintillator comprises a scintillator sheet comprising a proximal side nearer to the image sensor and a distal side disposed opposite to the proximal side, and wherein one or more of: the radiation source is secured to the distal side of the scintillator sheet; or the radiation source emits the energy into a positional channel, wherein the positional channel is disposed nearer to the distal side of the scintillator sheet such that the scintillator sheet is located between the image sensor and the positional channel.

Example 7 is a system as in any of Examples 1-6, wherein the radiation source comprises a plurality of radiation sources associated with a brachytherapy assembly, and wherein the system is configured for determining coordinates of the plurality of radiation sources during a procedure for administering radiation to a patient.

Example 8 is a system as in any of Examples 1-7, further comprising one or more processors in communication with the image sensor for executing instructions stored in non-transitory computer readable storage media, the instructions comprising: actuating the image sensor to capture a plurality of sequential image frames; assigning a timestamp to each of the plurality of sequential image frames; and calculating a velocity of the energy emitted by the radiation source based on the plurality of sequential image frames, wherein a position of the energy emitted by the radiation source is depicted in the plurality of sequential image frames as a scintillating region on the scintillator.

Example 9 is a system as in any of Examples 1-8, wherein the instructions further comprise: identifying one or more scintillating image frames each comprising one or more scintillating regions wherein the scintillator is scintillating absorbed energy; determining an intensity of the energy emitted by the radiation source based on the one or more scintillating image frames; and comparing the intensity to a known truth for the energy emitted by the radiation source based on a decay curve.

Example 10 is a system as in any of Examples 1-9, wherein the instructions further comprise: calculating a dwell time of the radiation source at a given location by summing one or more independent emissions of energy by the radiation source at the given location; and calculating a linearity of the intensity of the energy emitted by the radiation source based on the dwell time of the radiation source at a given location.

Example 11 is a system as in any of Examples 1-10, wherein the instructions further comprise calculating a total dose of radiation provided to the given location by summing one or more independent emissions of energy by the radiation source at the given location.

Example 12 is a system as in any of Examples 1-11, wherein the instructions further comprise calculating an ease of travel of the energy in an applicator, wherein the ease of travel is calculated based on a velocity of the energy through the catheter applicator.

Example 13 is a system as in any of Examples 1-12, wherein the radiation source comprises one or more of: a brachytherapy afterloader; a plurality of brachytherapy afterloader channels; or a bare source, wherein the bare source is not associated with a treatment delivery system.

Example 14 is a system as in any of Examples 1-13, further comprising one or more processors for executing an image processing algorithm on the image frame sensed by the image sensor, wherein the image frame comprises one or more scintillating regions where the scintillator is scintillating the absorbed energy, and wherein the image processing algorithm comprises: removing background elements from the image frame; calculating a contrast-to-noise ratio for the image frame; calculating pixel values for a plurality of pixels of the image frame; and cropping the image frame based on the contrast-to-noise ratio and the pixel values for the plurality of pixels of the image frame.

Example 15 is a system as in any of Examples 1-14, wherein the image processing algorithm is applied to a plurality of sequential image frames captured by the image sensor, and wherein the image processing algorithm further comprises: extracting image contours for the one or more scintillating regions of the image frame in each of the plurality of sequential image frames; and identifying a geometric center for each of the one or more scintillating regions in each of the plurality of sequential image frames.

Example 16 is a system as in any of Examples 1-15, wherein the image processing algorithm further comprises: identifying movement of the geometric center of each of the one or more scintillating regions across the plurality of sequential image frames; and calculating a velocity of the movement of the geometric center across the plurality of sequential image frames.

Example 17 is a system as in any of Examples 1-16, wherein the image processing algorithm further comprises: calculating an intensity value for pixels in the image frame;

calculating a cumulative intensity by summing the intensity value for the pixels in the image frame; identifying a scintillating region in the image frame; and calculating a cumulative intensity of the scintillating region in the image frame based on the intensity values for the pixels within the scintillating region.

Example 18 is a system as in any of Examples 1-17, wherein the image processing algorithm further comprises: identifying a fiducial marker on an absolute position marker, wherein the absolute position marker is disposed on a distal end of a positional channel configured for receiving the energy emitted by the radiation source, and wherein the proximal end of the positional channel comprises a radiation coupler for coupling the positional channel to the radiation source; registering a position of the fiducial marker in absolute coordinate space; and identifying a location of a scintillating region within the image frame in terms of the absolute coordinate space.

Example 19 is a system as in any of Examples 1-18, wherein the image sensor is synchronized with the radiation source such that the image sensor senses image frames only during one or more of: a time period corresponding with production of the energy by the radiation source; or a time period following the production of the energy by the radiation source.

Example 20 is a system as in any of Examples 1-19, further comprising a bandpass filter, wherein scintillated energy released by the scintillator passes through the bandpass filter before being sensed by the image sensor.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium, which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. The terms "modules" and "components" are used in the names of certain components to reflect their implementation independence in software, hardware, circuitry, sensors, or the like. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein purposes of illustration and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:
   an image sensor for sensing electromagnetic radiation;
   a scintillator, wherein the scintillator absorbs energy emitted by a radiation source and scintillates the absorbed energy;
   wherein the image sensor senses an image frame depicting at least a portion of the scintillator when the radiation source emits the energy, and wherein the image frame comprises an indication of where the energy is absorbed by the scintillator; and
   a positional assembly, wherein the positional assembly comprises:
      a positional channel comprising a proximal end and a distal end, wherein the proximal end is nearer the radiation source; and
      an absolute position marker disposed at the distal end of the positional channel.

2. The system of claim 1, further comprising an enclosure comprising an interior space, wherein the image sensor and the scintillator are disposed within the interior space of the enclosure, and wherein the enclosure prevents ambient light from reaching the image sensor or the scintillator such that the interior space is light-deficient.

3. The system of claim 2, further comprising an imager assembly comprising the image sensor and a lens, wherein the imager assembly is mounted to a wall of the enclosure, and wherein the imager assembly is disposed within the interior space of the enclosure.

4. The system of claim 1, wherein:
   the positional assembly further comprises a radiation coupler, wherein the radiation coupler is disposed at the proximal end of the positional channel for coupling the positional channel to the radiation source; and
   the positional channel comprises a hollow tube for communicating the energy emitted by the radiation source.

5. The system of claim 1, wherein the scintillator comprises a scintillator sheet comprising a proximal side nearer to the image sensor and a distal side disposed opposite to the proximal side, and wherein one or more of:
   the radiation source is secured to the distal side of the scintillator sheet; or
   the radiation source emits the energy into a positional channel, wherein the positional channel is disposed nearer to the distal side of the scintillator sheet such that the scintillator sheet is located between the image sensor and the positional channel.

6. The system of claim 1, wherein the radiation source comprises a plurality of radiation sources associated with a brachytherapy assembly, and wherein the system is configured for determining coordinates of the plurality of radiation sources during a procedure for administering radiation to a patient.

7. The system of claim 1, further comprising one or more processors in communication with the image sensor for executing instructions stored in non-transitory computer readable storage media, the instructions comprising:
   actuating the image sensor to capture a plurality of sequential image frames;
   assigning a timestamp to each of the plurality of sequential image frames; and
   calculating a velocity of the energy emitted by the radiation source based on the plurality of sequential image frames, wherein a position of the energy emitted by the radiation source is depicted in the plurality of sequential image frames as a scintillating region on the scintillator.

8. The system of claim 7, wherein the instructions further comprise:
   identifying one or more scintillating image frames each comprising one or more scintillating regions wherein the scintillator is scintillating absorbed energy;
   determining an intensity of the energy emitted by the radiation source based on the one or more scintillating image frames; and
   comparing the intensity to a known truth for the energy emitted by the radiation source based on a decay curve.

9. The system of claim 8, wherein the instructions further comprise:
   calculating a dwell time of the radiation source at a given location by subtracting a first timestamp wherein the scintillating region is deemed stationary from a final timestamp prior to the scintillating region no longer remaining stationary; and
   calculating a linearity of the intensity of the energy emitted by the radiation source based on the dwell time of the radiation source at a given location.

10. The system of claim 9, wherein the instructions further comprise calculating a total dose of radiation provided to the given location by summing one or more independent emissions of energy by the radiation source at the given location.

11. The system of claim 7, wherein the instructions further comprise calculating an ease of travel of the energy in a catheter applicator, wherein the ease of travel is calculated based on a velocity of the energy through the catheter applicator.

12. The system of claim 1, wherein the radiation source comprises one or more of:
- a brachytherapy afterloader;
- a plurality of brachytherapy afterloader channels; or
- a bare source, wherein the bare source is not associated with a treatment delivery system.

13. The system of claim 1, further comprising one or more processors for executing an image processing algorithm on the image frame sensed by the image sensor, wherein the image frame comprises one or more scintillating regions where the scintillator is scintillating the absorbed energy, and wherein the image processing algorithm comprises:
- removing background elements from the image frame;
- calculating a contrast-to-noise ratio for the image frame;
- calculating pixel values for a plurality of pixels of the image frame.

14. The system of claim 13, wherein the image processing algorithm is applied to a plurality of sequential image frames captured by the image sensor, and wherein the image processing algorithm further comprises:
- extracting image contours for the one or more scintillating regions of the image frame in each of the plurality of sequential image frames; and
- identifying a geometric center for each of the one or more scintillating regions in each of the plurality of sequential image frames.

15. The system of claim 14, wherein the image processing algorithm further comprises:
- identifying movement of the geometric center of each of the one or more scintillating regions across the plurality of sequential image frames; and
- calculating a velocity of the movement of the geometric center across the plurality of sequential image frames.

16. The system of claim 13, wherein the image processing algorithm further comprises:
- calculating an intensity value for pixels in the image frame;
- calculating a cumulative intensity by summing the intensity value for the pixels in the image frame;
- identifying a scintillating region in the image frame; and
- calculating a cumulative intensity of the scintillating region in the image frame based on the intensity values for the pixels within the scintillating region.

17. The system of claim 13, wherein the image processing algorithm further comprises:
- identifying a fiducial marker on an absolute position marker, wherein the absolute position marker is configured for receiving the energy emitted by the radiation source, and wherein the proximal end of the positional channel comprises a radiation coupler for coupling the positional channel to the radiation source;
- registering a position of the fiducial marker in absolute coordinate space; and
- identifying a location of a scintillating region within the image frame in terms of the absolute coordinate space.

18. The system of claim 1, wherein the image sensor is synchronized with the radiation source such that the image sensor senses image frames only during one or more of:
- a time period corresponding with production of the energy by the radiation source; or
- a time period following the production of the energy by the radiation source.

19. The system of claim 1, further comprising a bandpass filter, wherein scintillated energy released by the scintillator passes through the bandpass filter before being sensed by the image sensor.

20. A system comprising:
- an image sensor for sensing electromagnetic radiation;
- a scintillator, wherein the scintillator absorbs energy emitted by a radiation source and scintillates the absorbed energy;
- wherein the image sensor senses an image frame depicting at least a portion of the scintillator when the radiation source emits the energy, and wherein the image frame comprises an indication of where the energy is absorbed by the scintillator;
- wherein the system further comprises one or more processors in communication with the image sensor for executing instructions stored in non-transitory computer readable storage media, the instructions comprising:
- actuating the image sensor to capture a plurality of sequential image frames;
- assigning a timestamp to each of the plurality of sequential image frames; and
- calculating a velocity of the energy emitted by the radiation source based on the plurality of sequential image frames, wherein a position of the energy emitted by the radiation source is depicted in the plurality of sequential image frames as a scintillating region on the scintillator.

* * * * *